United States Patent
Hanlon, Jr. et al.

(10) Patent No.: US 11,417,429 B2
(45) Date of Patent: Aug. 16, 2022

(54) SYSTEM AND METHOD FOR PROVIDING WELLNESS RECOMMENDATION

(71) Applicant: CENTERLINE HOLDINGS LLC, Stroudsburg, PA (US)

(72) Inventors: Robert Paul Hanlon, Jr., Stroudsburg, PA (US); Monte Floyd Hancock, Jr., Murray, KY (US)

(73) Assignee: CENTERLINE HOLDINGS LLC

( * ) Notice: Subject to any disclaimer, the term of this patent is extended or adjusted under 35 U.S.C. 154(b) by 0 days.

(21) Appl. No.: 17/464,090

(22) Filed: Sep. 1, 2021

(65) Prior Publication Data
US 2022/0076834 A1 Mar. 10, 2022

Related U.S. Application Data

(60) Provisional application No. 63/150,402, filed on Feb. 17, 2021, provisional application No. 63/074,670, filed on Sep. 4, 2020.

(51) Int. Cl.
| | |
|---|---|
| *G16H 50/20* | (2018.01) |
| *G16H 40/67* | (2018.01) |
| *G16H 50/30* | (2018.01) |
| *G16H 50/70* | (2018.01) |
| *G16H 10/60* | (2018.01) |
| *G06Q 40/08* | (2012.01) |
| *G16H 20/70* | (2018.01) |
| *A61B 5/00* | (2006.01) |

(Continued)

(52) U.S. Cl.
CPC ............. *G16H 50/20* (2018.01); *A61B 5/165* (2013.01); *A61B 5/486* (2013.01); *G06Q 40/025* (2013.01); *G06Q 40/08* (2013.01); *G16H 10/60* (2018.01); *G16H 20/70* (2018.01); *G16H 40/67* (2018.01); *G16H 50/30* (2018.01); *G16H 50/70* (2018.01); *A61B 5/02438* (2013.01)

(58) Field of Classification Search
CPC ........ G16H 50/20; G16H 40/67; G16H 10/60; G16H 50/30; G16H 50/70; G16H 20/70; A61B 5/165; A61B 5/486; A61B 5/02438; G06Q 40/025; G06Q 40/08
USPC ........................................................ 705/2–3
See application file for complete search history.

(56) References Cited

U.S. PATENT DOCUMENTS

| | | |
|---|---|---|
| 9,396,486 B2 | 7/2016 | Stivoric et al. |
| 9,731,166 B2 | 8/2017 | Zhang et al. |

(Continued)

OTHER PUBLICATIONS

International Search Report and Written Opinion of PCT/US2021/048688 dated Dec. 17, 2021.

*Primary Examiner* — Michael Tomaszewski
(74) *Attorney, Agent, or Firm* — The Belles Group, P.C.

(57) ABSTRACT

In one embodiment, the present disclosure is directed to a method for providing a recommended wellness behavior. User data is received for different wellness components, the user data including data related to physical health, finances, and psychology. A user's wellness is assessed by, for each wellness component, determining a difference between the current user score and a relevant demographic standard, and determining a predicted future score based thereon. A recommended behavior is determined based on an identification of the wellness components having greatest differences between the predicted future score and the demographic standard. An indicator of the recommended behavior is then output to the user.

19 Claims, 15 Drawing Sheets

(51) Int. Cl.
*A61B 5/16* (2006.01)
*G06Q 40/02* (2012.01)
*A61B 5/024* (2006.01)

(56) References Cited

U.S. PATENT DOCUMENTS

| | | |
|---|---|---|
| 9,750,433 B2 | 9/2017 | Hu et al. |
| 9,842,313 B2 | 12/2017 | B'Far et al. |
| 9,990,471 B2 | 6/2018 | Prakash et al. |
| 10,558,916 B2 | 2/2020 | Hanlon |
| 10,614,724 B2 | 4/2020 | Catani et al. |
| 11,003,741 B2 | 5/2021 | Naik |
| 2014/0125480 A1 | 5/2014 | Utter, II |
| 2014/0125493 A1 | 5/2014 | Utter, II |
| 2014/0129242 A1 | 5/2014 | Utter, II |
| 2015/0088542 A1 | 3/2015 | Balassanian |
| 2015/0317446 A1* | 11/2015 | Ash ............ G16Z 99/00 705/2 |
| 2015/0347939 A1 | 12/2015 | King et al. |
| 2015/0356513 A1 | 12/2015 | Walkingshaw et al. |
| 2016/0171180 A1 | 6/2016 | Yagnyamurthy et al. |
| 2016/0203402 A1 | 7/2016 | Hanlon |
| 2017/0109479 A1* | 4/2017 | Vemireddy ............ G06Q 50/22 |
| 2017/0132395 A1 | 5/2017 | Futch |
| 2017/0300655 A1 | 10/2017 | Lane et al. |
| 2018/0218289 A1 | 8/2018 | Albrecht |
| 2018/0239874 A1 | 8/2018 | Ingram et al. |
| 2019/0110774 A1* | 4/2019 | Flynn ............ A61B 7/00 |
| 2020/0167815 A1 | 5/2020 | Naik et al. |
| 2021/0015415 A1 | 1/2021 | Ofir |
| 2021/0125699 A1 | 4/2021 | Vergara, Jr. |

\* cited by examiner

| | | | | | 79 |
|---|---|---|---|---|---|
| Name: | | Date: | | ☐ Morning  Evening ☐ | |

Psychological Twice-Daily Checklist Items

(Check a box in each row, or leave blank...)
( − means more negative feeling, + means more positive feeling, leave blank if "just OK")

− +

| | OK | | |
|---|---|---|---|
| ☐ | OK | Positivity: | I think today is a GOOD day! |
| ☐ | OK | Engagement: | I feel like I am part of what is going on around me today. |
| ☐ | OK | Relationships: | I am satisfied with my relationships with others today. |
| ☐ | OK | Meaning: | I believe that what I am doing today matters. |
| ☐ | OK | Accomplishment: | I feel GOOD about this week's plans and accomplishments. |
| ☐ | OK | Emo_Stability: | My emotions are stead and under control today. |
| ☐ | OK | Optimism: | I am looking forward to the rest of this week. |
| ☐ | OK | Resilience: | I am overcoming today's challenges. |
| ☐ | OK | Self_Esteem: | I feel GOOD about myself today. |
| ☐ | OK | Vitality: | I have plenty of energy today. |

In at most three words: Best thing about today ⇨ [          ]
In at most three words: Worst thing about today ⇨ [          ]

Physiological Twice-Daily Checklist Items

[      ] ⇦ Hours of Sleep in the last 12 hours (write in box)

[      ] ⇦ Blood Sugar (if measured) (write in box)    ☐ YES  NO ☐ Menstruating?

Total Calories consumed since waking up today: (check one box)
  ☐ 0 - 1000  ☐ 1000 - 2000  ☐ 2000 - 3000  ☐ Over 3000
Total Calories of Carbohydrates consumed since waking up today: (check one box)
  ☐ 0 - 1000  ☐ 1000 - 2000  ☐ 2000 - 3000  ☐ Over 3000

Financial Twice-Daily Checklist Items

(check one box in each row)
☐ YES  NO ☐ Short-term Savings: I have more than enough money to meet this month's expenses.
☐ YES  NO ☐ Budgeting: I am sticking to a budget today.

FIG. 8

SYSTEM AND METHOD FOR PROVIDING WELLNESS RECOMMENDATION

CROSS REFERENCE TO RELATED APPLICATIONS

The present application claims the benefit of U.S. Provisional Patent Application No. 63/074,670 filed on Sep. 4, 2020, and U.S. Provisional Patent Application No. 63/150,402 filed on Feb. 17, 2021. The disclosures of the aforementioned priority applications are incorporated herein by reference in their entireties.

BACKGROUND

Wellness has various components, and these components may be grouped into the categories of psychological wellness, physiological wellness, and financial wellness. Psychophysiological economic theory posits that these categories are interrelated, each affecting the others. For example, poor financial wellness can negatively impact psychological wellness, which in turn can affect physiological wellness, and so impact finances. The fact that these factors are affected by behavior implies that wellness can be proactively influenced by behavior. For example, improving financial wellness could, by means of interaction, lead to improvement in psychological and/or physiological wellness.

While the interactions between the wellnesses can be complex, they may be subject to analysis and modeling, and they may be purposefully influenced by personal choices and behavior. Assessment of wellness involves both objective and subjective metrics. Some wellness metrics (e.g., resting heart rate and total unsecured debt) can be directly measured and expressed in quantitative terms. Others (e.g., psychological stress level and sense of well-being) are expressed in qualitative terms, but can be quantified by means of objective proxy variables (e.g., heart-rate variability and Cortisol level), and/or by principled probability distributions.

Present technologies are fragmented and unintegrated, not providing unified, consistent, comprehensive, or real-time advice. What is needed is a technology that captures the major determinants of health (social, financial, physical, psychological) and measures and manages them across the three main wellness categories using individualized calculations for optimization. It is further needed for the technology to be agnostic towards both hardware and enterprise platforms so that it can be hosted seamlessly across a multitude of platforms.

BRIEF SUMMARY

The present disclosure may be directed, in one aspect, to a method for providing a recommended wellness behavior, the method comprising: a) receiving, for a user, user data for different wellness components, the user data comprising: i) device data obtained from a wearable device, the device data being indicative of a physical health status and a stress status of the user; ii) financial data for the user; and iii) psychological data for the user; iv) wherein the user data includes current data and historical data; b) receiving at least one user behavior preference indicative of a preferred recommended behavior; c) receiving demographic standards for the different wellness components; d) assessing the user's wellness by: i) for each wellness component, determining a current user score based on the received user data; ii) for each wellness component, determining a difference between the current user score and the demographic standard; iii) for each wellness component, using a recursive algorithm to: 1) determine a predicted future score based on (a) the current user score; (b) the difference between the current user score and the demographic standard; and (c) a controller coefficient that depends on a demographic for the user; and 2) determine a difference between the predicted future score and the demographic standard; e) identifying at least one recommended behavior based on: i) an identification of the wellness components having greatest differences between the predicted future score and the demographic standard; and ii) the at least one user behavior preference; and f) outputting an indicator of the at least one recommended behavior; g) wherein the foregoing operations are performed by one or more processors.

In another aspect, the present disclosure may be directed to a method for providing a recommended wellness behavior, the method comprising: a) receiving, for a user, user data for different wellness components, the user data comprising: i) device data obtained from a wearable device, the device data being indicative of a physical health status or a stress status of the user; ii) financial data for the user; and iii) psychological data for the user; b) receiving demographic standards for the different wellness components; c) assessing the user's wellness by: i) for each wellness component, determining a current user score based on the received user data; ii) for each wellness component, determining a difference between the current user score and the demographic standard; iii) for each wellness component, determining a comparison score based on the current user score; d) identifying at least one recommended behavior based on an identification of the wellness components having greatest differences between the comparison score and the demographic standard; and e) outputting an indicator of the at least one recommended behavior; f) wherein the foregoing operations are performed by one or more processors.

In another aspect, the present disclosure may be directed to a system for providing a recommended wellness behavior, the system comprising: a) a wearable device configured to obtain device data indicative of a physical health status and a stress status of a user; b) a server configured to carry out the operations of: i) receiving user data for different wellness components, the user data comprising: 1) the device data; 2) financial data for the user; and 3) psychological data for the user; 4) wherein the user data includes current data and historical data; ii) receiving at least one user behavior preference indicative of a preferred recommended behavior; iii) receiving demographic standards for the different wellness components; iv) assessing the user's wellness by: 1) for each wellness component, determining a current user score based on the received user data; 2) for each wellness component, determining a difference between the current user score and the demographic standard; 3) for each wellness component, using a recursive algorithm to: (a) determine a predicted future score based on (i) the current user score; (ii) the difference between the current user score and the demographic standard; and (iii) a controller coefficient that depends on a demographic for the user; and (b) determine a difference between the predicted future score and the demographic standard; v) identifying at least one recommended behavior based on: 1) an identification of the wellness components having greatest differences between the predicted future score and the demographic standard; and 2) the at least one user behavior preference; and vi) outputting an indicator of the at least one recommended behavior.

In another aspect, the present disclosure may be directed to a system for providing a recommended wellness behavior, the system comprising: a) a wearable device configured to obtain device data indicative of a physical health status or a stress status of a user; b) a server configured to carry out the operations of: i) receiving user data for different wellness components, the user data comprising: 1) the device data; 2) financial data for the user; and 3) psychological data for the user; ii) receiving demographic standards for the different wellness components; iii) assessing the user's wellness by: 1) for each wellness component, determining a current user score based on the received user data; 2) for each wellness component, determining a difference between the user score and the demographic standard; 3) for each wellness component, determining a comparison score based on the current user score; iv) identifying at least one recommended behavior based on an identification of the wellness components having greatest differences between the comparison score and the demographic standard; and v) outputting an indicator of the at least one recommended behavior.

BRIEF DESCRIPTION OF THE DRAWINGS

The present disclosure will become more fully understood from the detailed description and the accompanying drawings, wherein:

FIG. 8 is an example checklist to be completed by a user.

Figure 1:
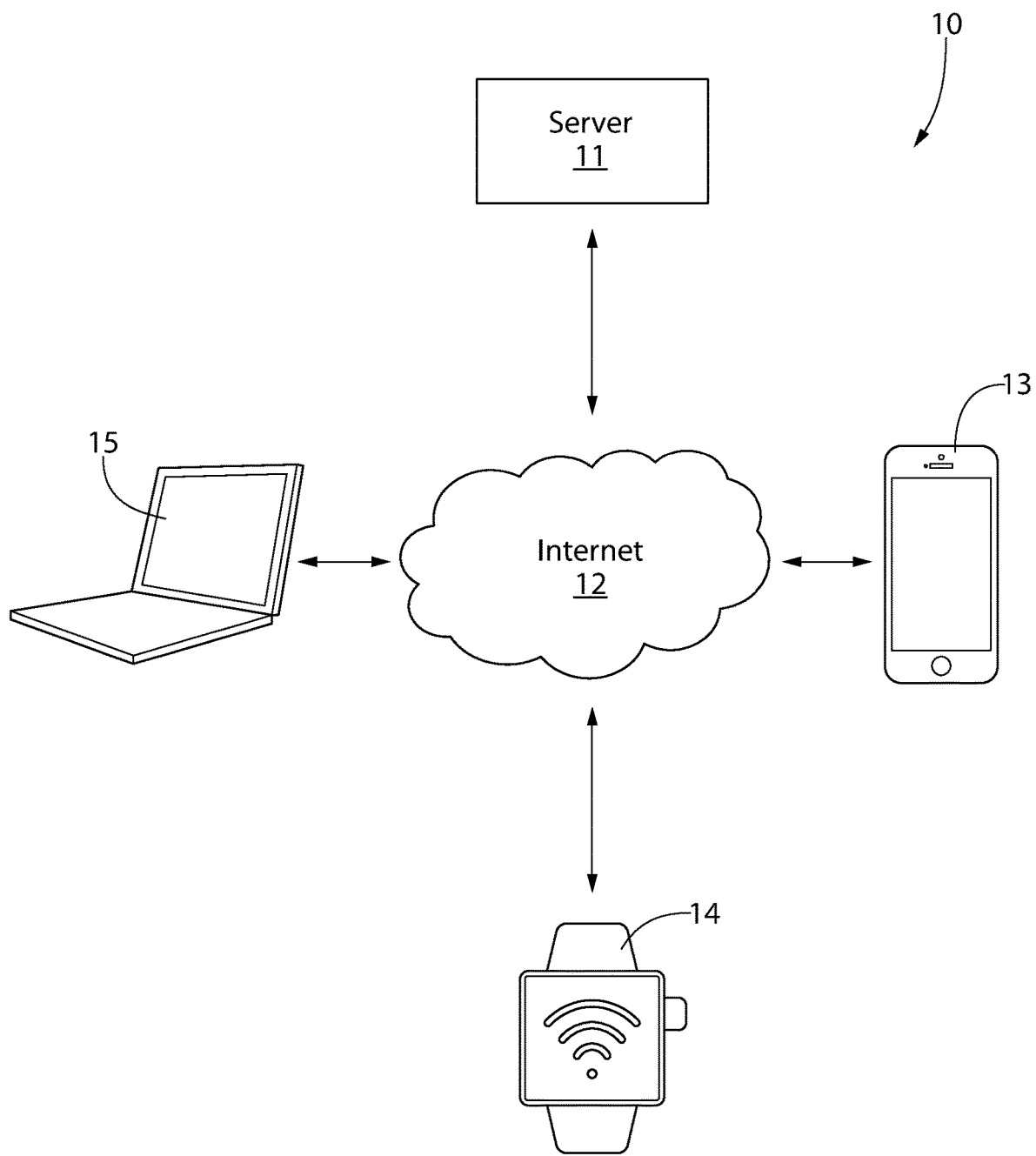
FIG. 1 is a block diagram of a system according to one embodiment.

The drawings represent one or more embodiments of the present invention(s) and do not limit the scope of invention.

DETAILED DESCRIPTION

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to the interpretation "based entirely on."

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Where block diagrams or circuits are shown and described, one of skill in the art will recognize that, for the sake of clarity, not all peripheral components or circuits are shown in the figures or described in the description. For example, common components such as memory devices and power sources may not be discussed herein, as their role would be easily understood by those of ordinary skill in the art. Further, the terms "couple" and "operably couple" can refer to a direct or indirect coupling of two components of a circuit.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present inventions may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Disclosed herein is a system and method by which the wellness of individuals can be assessed and enhanced. Data may be processed using multiple software systems, disparate hardware devices, and network communication systems to create a novel recommender system in support of human wellness. U.S. Pat. No. 10,558,916 is incorporated herein by reference in its entirety.

Referring now to the figures, FIG. 1 is a block diagram of a system 10 according to one embodiment. The exemplified system 10 includes a server 11 operably coupled to the internet 12, as well as various user devices 13, 14, 15 operably coupled to the internet, and thereby coupled to the server. The server 11 (and other servers discussed herein) can be any computer or processor (or collection thereof) for carrying out programs in accordance with the functions described herein. In the exemplified embodiment, the server 11 communicates with the devices 13, 14, 15 through the internet. The server 11 can communicate with the devices 13, 14, 15 through any standard communication means, including through use of a telecommunication network (e.g., 3G or 4G), Wi-Fi, or a wired internet connection (e.g., wired Ethernet cables).

As shown in FIG. 1, the user device may be a wearable device such as a smartwatch 14. In other embodiments, the wearable device may be eyewear, smart clothing, a wearable camera, a wearable medical device, smart jewelry, am implantable, or some other type of device worn by or otherwise carried by the user. User devices may also include a smartphone 13, a computer 15, or any other computer device capable of carrying out programs in accordance with the functions described herein (including desktop computers and tablets).

In certain embodiments, the system includes interoperable software, hardware, and network components that together implement the method to provide service on a subject-by-subject basis. It may include two subsystems: (1) Subject Application Processor (SAP) that is installed and operating on subject's/advisor's computing equipment (such as devices 13, 14, 15), and (2) Cloud-Based Processor (CBP), a cloud-based system (such as server 11) which receives/ collects subject information, and processes it to produce and serve information products to the subject (account information, recommendations, information products) through the SAP interface. The SAP may interface with metric devices and other information sources to obtain metric indicators bearing on the subject's wellness state (e.g., physiological measurements, lifestyle surveys). Further, the CBP may interface electronically with information sources bearing on the subject's wellness state (e.g., account activity, financial data).

Method

Figure 2:
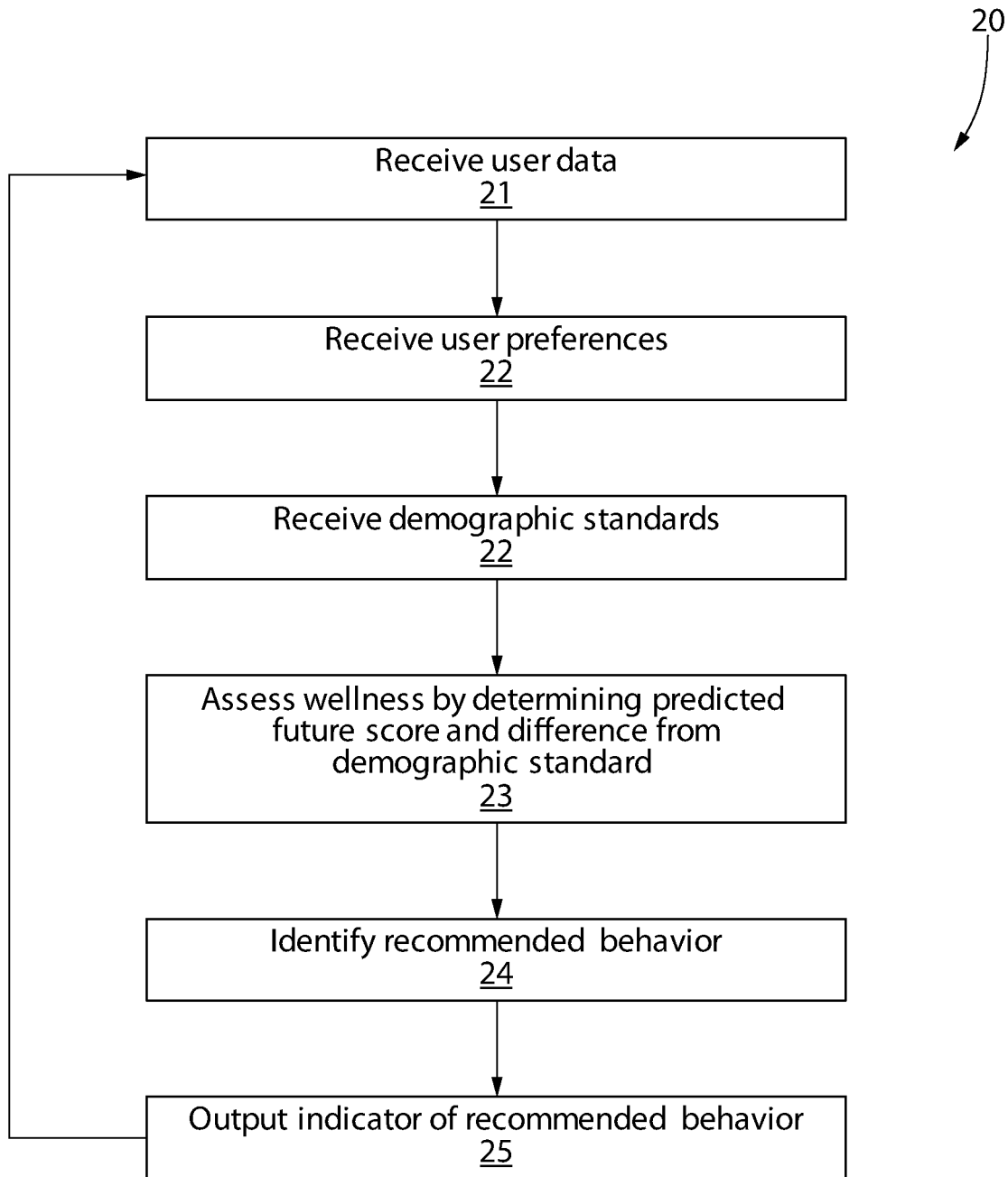
FIG. 2 is flowchart of a method of providing a recommended wellness behavior according to one embodiment.

FIG. 2 is flowchart of a method 20 of providing a recommended wellness behavior according to one embodiment. According to the exemplified method 20, in a first operation 21, user data is received for different wellness components. The exemplified user data may include real-time data obtained from a wearable device, the real-time data indicative of a physical health status and a stress status of the user. The user data further includes financial data for the user and psychological data for the user. The user data includes current data and historical data, though the invention is not so limited.

In operation 22, one or more user behavior preferences are received. These user behavior preferences are indicative of a preferred recommended behavior. For example, while the system may have several possible recommendations to provide for alleviating stress, the system can factor in the user's preferences in choosing a recommendation to provide. One user may prefer a type of breathing exercise, while another user may prefer a mindfulness exercise. Providing a recommended behavior that corresponds with the user's preferences helps to ensure that the user carries out the recommended behavior. In other embodiments, the use of user behavior preferences may be omitted.

In operation 23, demographic standards for the different wellness components are received. These demographic standards can provide standard values for each wellness component for each of different demographics. In this sense, the system can take into consideration that users in different life circumstances will not be expected to have similar scores for each of the wellness components.

In operation 24, the user's wellness is assessed. In the exemplified embodiment, this is carried out by, for each wellness component, determining a current user score based on the received user data. Methods for determining such a score are discussed in more detail below. For each wellness component, a difference is then determined between the current user score and the demographic standard. This difference may be determined using bias-based reasoning, as discussed in greater detail in the section entitled Bias-Based Reasoning.

Further, for each wellness component, a controller comprising a recursive algorithm determines a predicted future score based on (a) the current user score; (b) the difference between the current user score and the demographic standard; and (c) a controller coefficient that depends on a demographic for the user. Next, the recursive algorithm determines a difference between the predicted future score and the demographic standard. In the exemplified embodiment, the recursive algorithm is carried out by a proportional-integral-derivative (PID) controller, though the invention is not so limited. Further, each controller coefficient is different for each wellness component and is determined to scale an output of the controller. The controller coefficient, discussed in further detail below, is sometimes referred to as "inertia."

At least one recommended behavior is identified based on (a) an identification of the wellness components having greatest differences between the predicted future score and the demographic standard; and (b) the at least one user behavior preference. The recommended behavior may also be based on past user recommendations, their effectiveness, and the user's history of following (or not following) the recommendation. The identification of the recommended behavior may further utilize bias-based reasoning, as described in the section below entitled Bias-Based Reasoning.

In operation 25, an indicator of the at least one recommended behavior is output. This recommendation may be communicated, for example, in a report (such as that shown below) or in a message (e.g., an SMS message or email). In other embodiments, haptics may be used, for example, for assisting users with breathing techniques for stress mitigation. For example, a wearable device can vibrate to tell a user to look at the user's app, which can indicate that the user's heart rate is high and/or the user's heart rate variability (HRV) is low, and can provide explanations for the issue. The haptics can also vibrate to coach a user through a breathing technique that will help the user. Thus, the recommended behavior may be communicated to the user via a wearable device such as a smart watch.

The foregoing operations may be repeated in real-time to provide the user on-going real-time recommendations. These operations may be performed by one or more processors. In the exemplified embodiment, the operations are carried out by server 11 of FIG. 1, which comprises one or more processors. In other embodiments, the system need not provide real-time recommendations (or rely upon real-time data), but can instead provide reports or recommendations at specific times and/or for times past.

It is noted that a predicted future score need not be utilized. In other embodiments, another type of comparison score may be used, with the identification of the recommended behavior being based on an identification of the wellness components having greatest differences between the comparison score and the demographic standard. In certain embodiments, the comparison score may be the current user score itself. In other embodiments, the comparison score may be another score based on the current user score, such as an average of prior current user scores. In yet other embodiments, the comparison score is the predicted future score discussed above.

In other embodiments, the invention may be described as proceeding in cycles that consist of the following six operations: The method may be described as proceeding in cycles. Each cycle consists of six sequential steps: (1) Collect metrics for the subject (including history of past states and subject compliance). (2) Infer from metrics an assessment of the subject's current wellness state in each wellness component. (3) Compare the subject's current wellness state components to a customizable wellness standard to identify shortfalls. (4) Adjudicate the subject's wellness shortfalls by applying expert knowledge, informed by the subject's goals, to determine which shortfalls to address. (5) Apply expert knowledge to formulate a regimen of specific recommended behaviors which, if performed by the subject, will move the subject's wellness state toward their wellness target (their "Centerline"), or, sustain their state of wellness ("homeostasis"). (6) Create estimates of future wellness states under the assumption that recommended behaviors are performed by subject.

Data and Data collection

The wellness components may include one or more of the following:

Psychological:
Positivity=wellness 1
Engagement=wellness 2
Relationships=wellness 3
Meaning=wellness 4
Accomplishment=wellness 5
Emotional_Stability=wellness 6
Optimism=wellness 7
Resilience=wellness 8
Self Esteem=wellness 9
Vitality=wellness 10
Physical:
weight=wellness 11
BP=wellness 12
Sugar=wellness 13
Heart_Rate=wellness 14
Age=wellness 15
Sleep=wellness 16
Diet=wellness 17
Financial:
Spend<Earn=Spending is less than income=wellness 18
Timely_Bills=Pay all bills on time=wellness 19
Short_Savings=Sufficient liquid savings=wellness 20
Long_Savings=Sufficient long term savings=wellness 21
Managed_Debt=Manageable debt load=wellness 22
Solid_Credit=Prime credit score=wellness 23
Insured=Have appropriate insurance=wellness 24
Expense_Plan=Plan ahead for expenses=wellness 25

Various means may be used to collect subject wellness metrics, including subjective instruments such as regular subject surveys, periodic structured interviews conducted by an expert; and objective instruments such as physical monitors (heart-rate, blood sugar, blood pressure), and access to online information sources (e.g., financial accounts). The SAP is one means by which certain metrics are collected and uploaded to the cloud-based system. The CBP is one means by which certain metrics are collected from online sources on the subject's behalf.

Service models may include Direct-to-User and Advisor-Mediated. Direct-to-User service involves no middle-man. The subject subscribes for service, provides metric information and permissions to the system, and receives reports (account information, recommendations, information products). Advisor-Mediated service, by contrast, is provided through a professional mediator who manages the service on the subject's behalf, using the information products provided by the system to advise the subject.

The technologies described herein have several potential commercial applications, such as the following: sold as a service direct-to-users, and sold as a tool to advisory service providers; financial planners to use with their clients for life planning and life coaching; corporate wellness program to encourage, monitor, and enhance employee wellness; digital health platforms to augment their offering either in telemed, telepsych, or telefinance to provide an artificial intelligence (AI) conduit of care for users across three wellness categories such that if a health concern or breach is triggered then real life doctors, psychologists and financial planners can engage for care at cost to either the insurer, the user or corporate; and data marketplace for users to be able to sell their personal data to clinical research organizations or insurers.

A person could be eligible for a discount on health insurance, life insurance, or a mortgage rate based on using the system or having their numbers hit certain thresholds. Costs could change based on ongoing monitoring. Could also impact employee compensation.

Exemplary method for Assessment, Forecasting, and Recommendation

The following will describe an exemplary method for assessment, forecasting, and recommendation using the 25 wellness components discussed above. Each of the 25 wellness components has been assigned a numeric target value (the "Centerline" for that factor) using norms obtained from national health databases. Using these target values as vector components, a 25-dimensional Centerline wellness vector is established. (In an alternative embodiment, the system maintains a centerline wellness vector for each of 8 standard demographics based upon age, gender, and marital status.)

Using the current wellness metrics for a subject as vector components, a 25-dimensional state vector is obtained. Each is multiplied by a corresponding numeric weight according to its importance in assessing overall wellness.

Assessment of the subject's current wellness is performed by computing an aggregate wellness score based upon their wellness metrics, and the centerline for their demographic. The aggregate wellness score for a subject is given by the "distance" or difference between the subject state vector and the centerline wellness vector for the subject's demographic. Smaller distance corresponds to greater wellness. Distance is selectable among, L1, L2, and Cosine distance, giving three different ways to roll up an aggregate wellness.

The subject's wellness state is updated during each processing cycle. This creates a sequence of points in the 25-dimensional wellness space. Viewed as a function of time, this establishes a "wellness trajectory" for the user. In this view, the system can be thought of as a feedback control system. The subject is moving along a trajectory through the wellness space, attempting to achieve homeostasis. The system provides recommended behaviors intended to nudge the subject toward homeostasis.

An analogy is the cruise control of a car. The vehicle is on a trajectory. The driver selects a setpoint (desired speed), and the throttle of the car nudges the vehicle toward the desired speed. Actual speed is fed-back to the system through the speedometer. The new state is assessed. New control inputs are made, and the loop continues.

The exemplified embodiment uses a classic feedback control loop algorithm called a Proportional-Integral-Derivative, or PID controller. This embodiment uses a separate PID controller for each metric component: 25 independent controllers operating in real-time, to forecast the subject's wellness trajectory into the future. In the exemplary embodiment, the forward projections are only used to evaluate the recommendations made, and the subject's compliance with them. By using studies of human subjects, these projections, which estimate the likely effectiveness of system recommendations, may be incorporated into the recommender system.

The system maintains a "wellness trajectory" for the user as a time-sequence of points in a 25-dimensional wellness space, where each dimension is the numeric value of the corresponding wellness component. The wellness predictions are retrospective. The PID controller predicts future scores in each of the 25 wellness components based upon the entire wellness trajectory, and the controllability (henceforth referred to as the "inertia" or a "controller coefficient") of each wellness component. Inertia can be thought of as a measure of how rapid and effective user behavior for this demographic is in affecting the corresponding wellness component. In certain embodiments, the system projects the numeric values of each component forward under the assumption that the inertia of each component remains constant. The numeric values of the demographic inertias for each of the 25 wellness components are part of the characterization of the demographic. Certain embodiments may include customization and personalization of the wellness inertia values for the demographics, and for individual users.

The recommendations may be provided to the subject/advisor in the form of a prose report. This report describes the subject's current wellness state with respect to their centerline wellness; performs information fusion to determine which wellness factors are most in need of remediation; and writes a recommendation report containing specific recommended actions for the subject, and explaining why they are important. The information fusion algorithm takes into account the specific goals of the subject, and their likelihood of compliance. The fusion is performed by a knowledge-based expert system (KBES). This is a system containing expert-level human knowledge in the form of heuristics (rules) emulating the thought process of the human expert.

A report template includes slots for recommendation inputs. A repository of recommendations from national health websites is held as a database. A second knowledge-based expert system (KBES) ingests the subject current state and assessment, and selects recommendations to be inserted into the report template. Summary statistics and explanations of the recommendations are dropped into the report as well. The resulting report is an emulation in both content and appearance of a report that would be prepared by human experts to service the subject's wellness needs. A sample report is provided below in the section entitled Data Conformation.

The difference between the user score and the demographic standard is a deviation from the wellness centerline for the user. It is the relative size and significance of this deviation that is used by the KBES to determine which wellness components are in greatest need of remediation. The system could make recommendations for every area in which there is deviation from centerline wellness, but humans will not comply with a long list of recommended behaviors. The difference is used to sort the list of possible recommendations so that the few most important (and most likely to be implemented by the user based upon their history, goals, and preferences) are included in the recommendation.

The foregoing system utilizes a novel machine learning approach. The KBES are not hard-coded programs, but actually learn how to emulate human experts using supervised learning. The modified gradient ascent algorithm is described in some detail below in the section entitled in the Bias-Based Reasoning.

Past User Recommendations

The system may consider past user recommendations. The sequence of past user recommendations provides two important facts: (1) Is the current wellness strategy effective, in the sense that it is efficiently helping the user achieve and maintain their centerline? If so, it should be maintained. If not, future recommendations should consider a different recommendation strategy for this user in the under-performing areas. (2) Based upon surveys, user interviews, and collected data, is the user complying with the recommendations being made? If not, future recommendations should consider a different recommendation strategy for this user in the under-performing areas.

Recommendation strategies may be demographic-specific recommendation patterns maintained as data templates. These are recommendation reports that the Recommender KBES completes by filling in sentences and paragraphs to create a personalized recommendation for a specific user. At the time a recommendation is to be generated, an appropriate demographic-specific template is selected for the user based upon surveys, user interviews, collected data (biometric and online sources), and user history.

The exemplary system currently supports eight demographics: Young Unmarried Male, Older Unmarried Male, Young Unmarried Female, Older Unmarried Female, Young Married Male, Older Married Male, Young Married Female, Older Married Female. The number and constituent attributes of the demographics will be expanded and refined during system development. Constituent attributes to be added include psychological, physiological, and financial attributes of users. The specifics will be determined by applying data science techniques (e.g., supervised and unsupervised machine learning) to the user population.

Feedback Control for Optimizing Health Wellness

An exemplary method for feedback control will now be discussed in greater detail. A person's Centerline Wellness is the collection of their numeric wellness values in the wellness components listed above. Initially, target values (Centerline Wellness values) will be established by the judgement of domain experts in each wellness area, by reference to the published literature and population norms, and by one or more empirical case studies.

Figure 3:
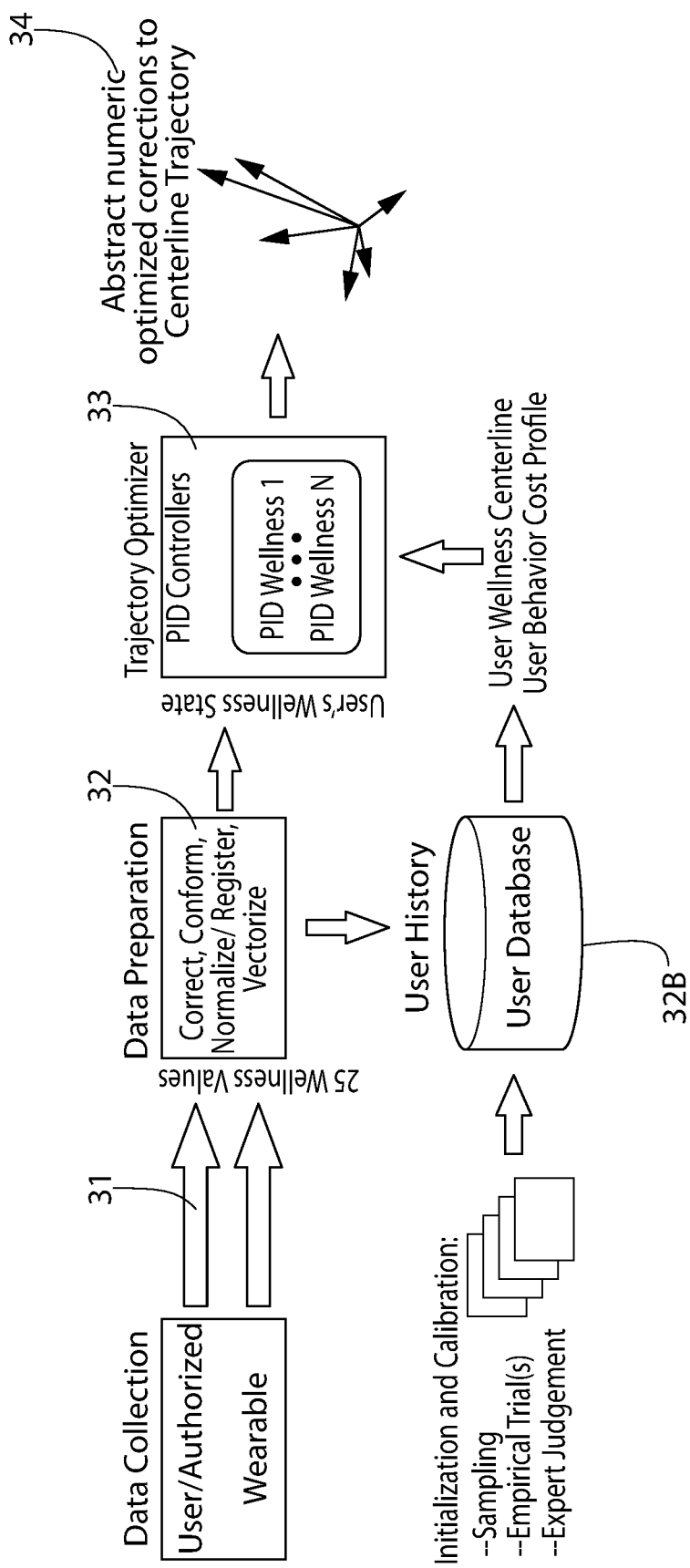
FIG. 3 is a flowchart of a method of abstract data processing according to one embodiment.
Figure 4:
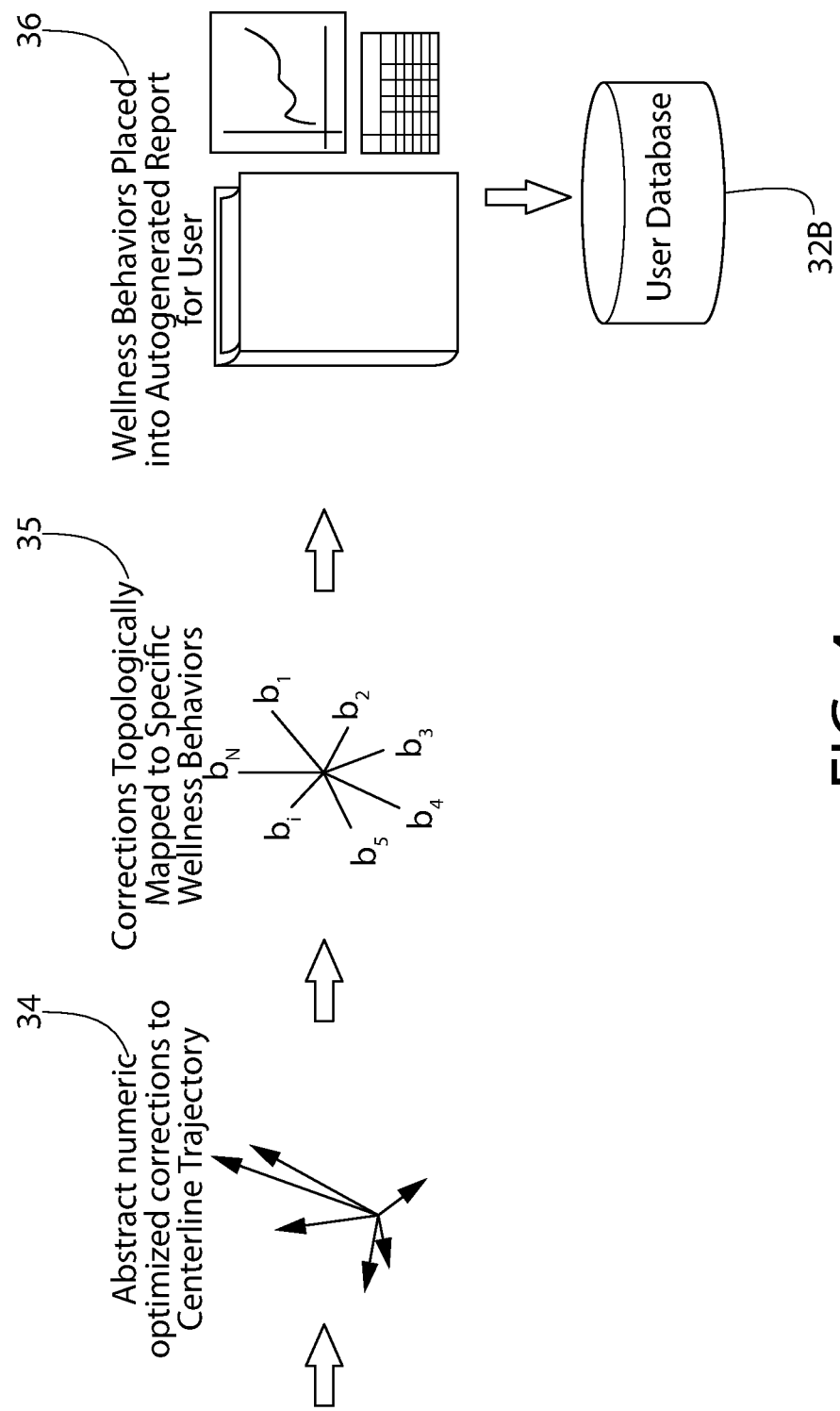
FIG. 4 is a flowchart of a method of knowledge-intensive analytic processing according to one embodiment.

Referring now to FIGS. 3 and 4, servicing Centerline Users is a linear process conducted in two phases. FIG. 3 shows Phase 1, which includes abstract data processing. FIG. 4 shows Phase 2, which includes knowledge-intensive analytic processing.

Raw data for a person's instantaneous wellness state (a vector of their wellness values) will be collected/inferred from information they provide, information collected from sources authorized by the user, and from one or more wearable devices on the user's person (operation 31).

This raw data will be conditioned and converted into a set of deviations from the person's Centerline Wellness (operation 32). Because the various wellness factors impact the user's life in different ways, and by different amounts, and with different latencies, the aggregate deviation from Centerline Wellness will be a weighted sum of the wellness deviations. Both instantaneous and long-term average wellness values will be created.

Given the deviation from Centerline Wellness, a collection of PID controllers 33 will determine the correcting signals 34 needed to restore the person to their Centerline Wellness. These correcting signals are abstract numeric representations of the adjustments needed to return the user's to a Centerline Trajectory in the Wellness state space. User history is saved in the user database 32B To make the abstract adjustments actionable, they must be translated into a coherent, comprehensible set of recommended behaviors 35. These specific recommended behaviors are then placed into an auto-generated report 36, which are saved in user database 32B. The intention is that, by undertaking the recommended behaviors, the user's deviation from Centerline Wellness will be reduced over time to nominal levels. The software we have implemented is referred to in this section as the Recommender.

Figure 5:
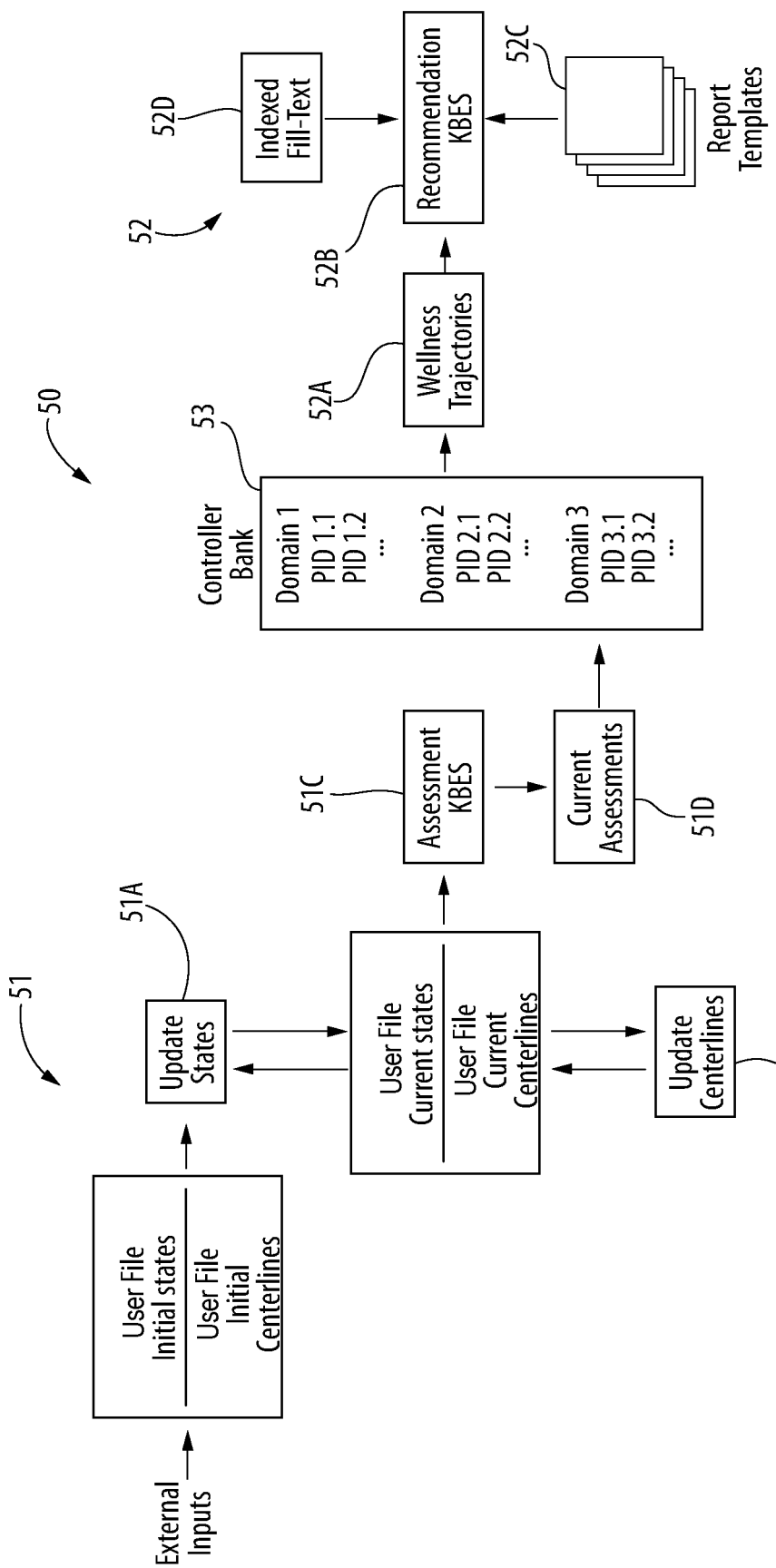
FIG. 5 is a block diagram of a recommender system according to one embodiment.

As shown in FIG. 5, the exemplified Recommender 50 uses two knowledge-based expert systems 51, 52 and a bank of 25 PID controllers 53 to determine whether and how wellness can be restored to a homeostatic set point using a closed-loop controller. The exemplified use case for this Recommender 50 employs two expert systems 51, 52, and a PID controller bank 53. The first expert system 51 assesses the user wellness state; the second expert system 52 formulates recommendations (in colloquial natural language) that address the user's demographic, and areas of greatest deviation from wellness; and the PID controllers 53 project the user state forward in time to characterize the benefits of following the recommendations. Two compliance factors specific to the individual user are applied to select recommendations most likely to be adopted by the user.

In expert system 51, external inputs are provided for the User file initial states and centerlines. The states are updated (operation 51A), as are the centerlines (operation 51B). The assessment KBES 51C provides current assessments 51D, which are provide to the PID controllers 53. In expert system 52, the recommendation KBES 52B receives wellness trajectories 52A from the PID controllers 53. The recommendation KBES 52B receives report templates 52C and indexed fill text 52D. While the approach of expert system 51 allows the determination of the kinds of corrections that are required in a vector space sense, it is still necessary to determine what specific real-world actions must be undertaken to produce the indicated changes. This will be accomplished by the recommendation KBES 52B.

Different users will experience levels of difficulty carrying out specific recommendations. This means that the "terrain of action" will be specific to the individual: what is difficult ("uphill") for one person might be relatively easy ("level or downhill terrain") for another. Therefore, the recommendations ("control signals") offered to move a person back to their centerline are individual in nature. These can be individualized over time. Initially, population norms can be used to establish these factors.

Figure 6:
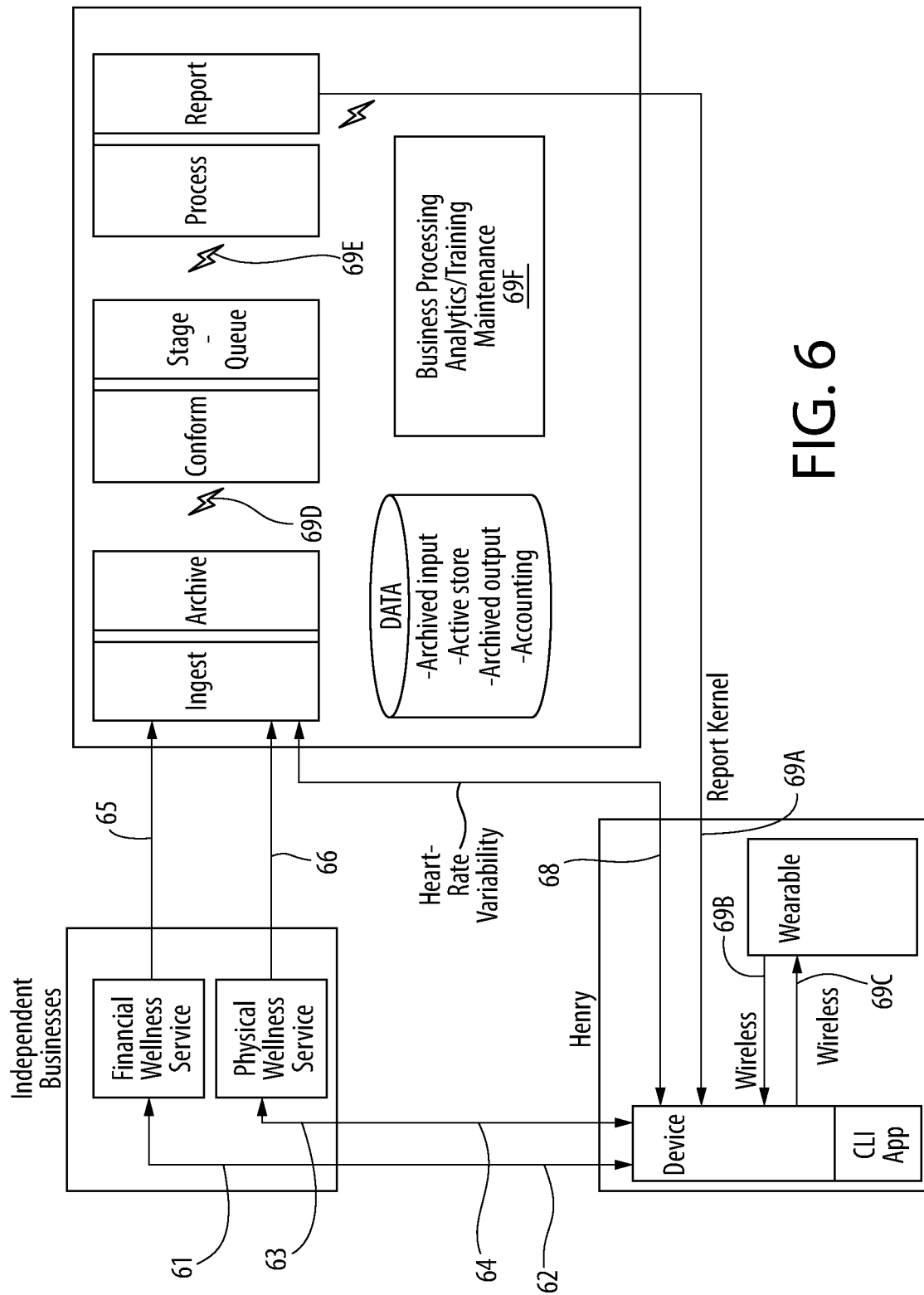
FIG. 6 is a system functional architecture according to one embodiment.

FIG. 6 is a system functional architecture according to the exemplified embodiment. This embodiment is hosted on the web, and has a simple web-accessible user interface that facilitates data input and the delivery of reports created by the Recommender. HENRY is the example user. Independent Businesses are independent service applications that currently contract with the user to provide information services using as input data uploaded synchronously/asynchronously by users through an HMI web interface. CLI (the operator of the exemplified system) will partner with some set of these to provide to CLI the information they currently serve to their population of users.

The user side of the web interface resides on the user's computer. The CLI App data and software reside on the user computer. Embedded data collection functionality resides on a User-wearable device. Data are exchanged synchronously/ asynchronously wirelessly between the CLI App on the user Computer and the User-Wearable device (operations 10 and 11).

In operation 61, a user provides financial wellness data to the Financial Wellness Service. In operation 62, financial wellness data is output to the user's CLI application (app). This financial wellness output may be provided by the Financial Wellness Service, which may comprise, for example, certified advisors or wellness engineers.

In operation 63, a user provides physical wellness data to the Physical Wellness Service (e.g., data manually entered by the user during brief, regular surveys conducting on the user's online device). In operation 64, physical wellness data is output to the user's CLI app.

In operation 65, the financial wellness data is output to the CLI Cloud-Based Processor (which may have a function similar to server 11 of FIG. 1). Such data could be indicative of annual income, credit score, short save, long save, health insurance, life insurance, budgeting, mortgage debt, college debt, non-educational unsecured debt, etc.

In operation 66, physical wellness data is output to the CLI Processor. In operations 67 and 68, heart-rate variability data (obtained, for example, by a wearable) are provided to the CLI Processor and the CLI app, respectively. In operation 69, a report is provided to the CLI app. Operations 69D and 69E are comparable to operations 31-36 of FIGS. 3-4. Finally, in operation 69F, the processed data is used for business processing analytics and training maintenance.

The implemented software starts with data input after login. The information required for the Knowledge Based Expert System to work is split into two parts: 1) some demographic information about the person to be evaluated, and 2) the measurement, score of importance, and score of compliance for each component in 3 wellness domains.

The demographic information is used to determine the ideal value of each component and the set of suitable recommendations and an action plan tailor made for the user. Important information that heavily influences the outcome by the algorithms can include, for example, age, marital status, and gender.

KBES can operate with incomplete input data, so the measurement of each component of all wellness domains is not required. However, measuring more components will increase the fidelity of system recommendations. In the exemplified embodiment, the software requires direct input from the users. The system can also take measurements directly from wearable health devices or obtain the score by presenting the user a survey. A received score of "importance" for each wellness component reflects how important the user subjectively thinks the component contributes to his or her overall wellbeing. A received score for "compliance" is the computed probability that a user may follow the recommendation given by the system to improve the overall wellness. The system may accept direct input, or this can be computed automatically by the system basing on the frequency of the user following the recommendation in the final product.

The information is sent to the algorithm after collection to go through an evaluation engine, which gives a diagnosis on each wellness component, and a recommendation engine, which gives a recommendation to improve each wellness domain by targeting the most urgent, i.e. influential, component to be improved within. The recommendation engine also provides a forecast that shows the percentage of improvement the user will have over a period of time if he or she follows the given recommendation.

Figure 7:
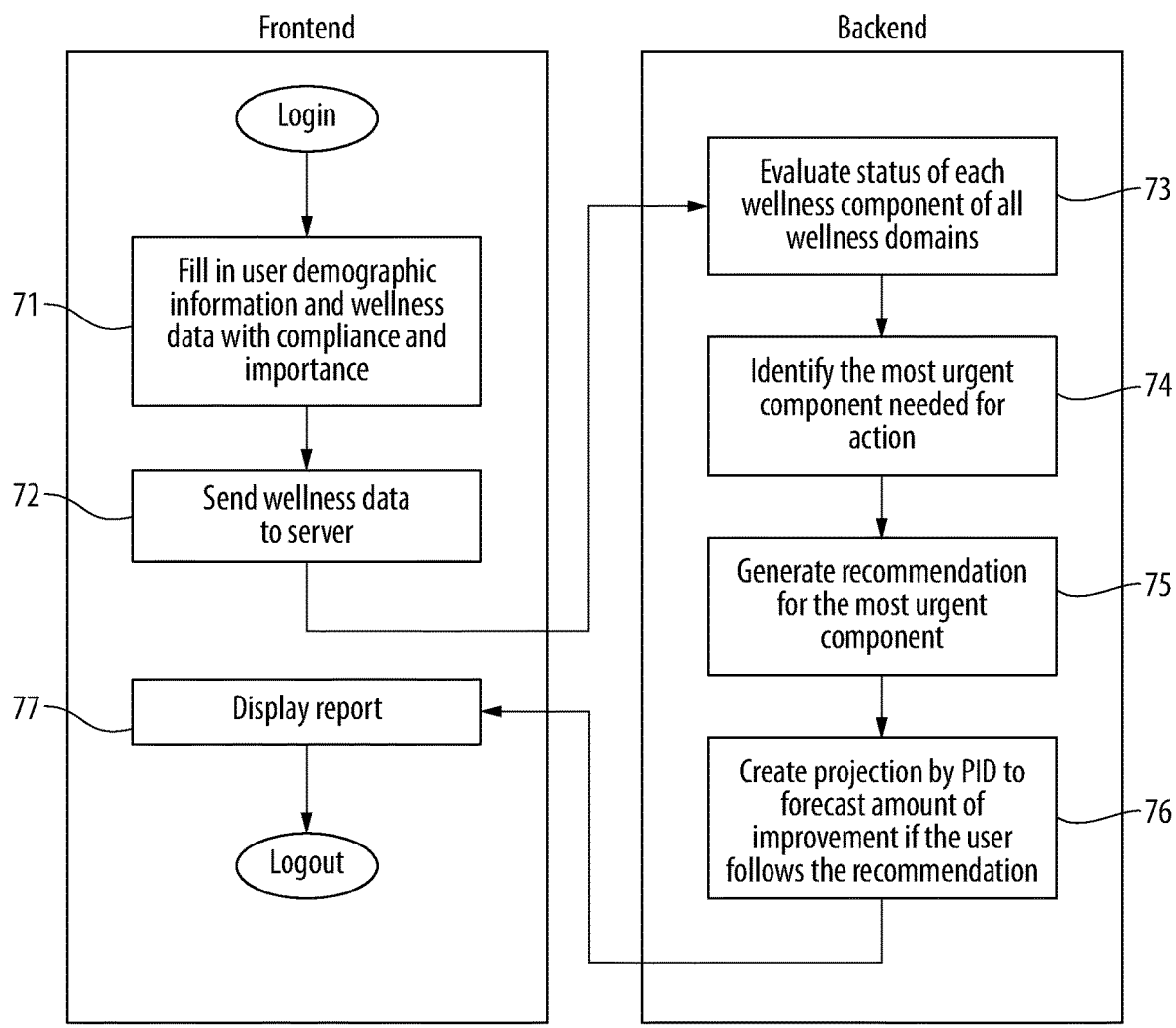
FIG. 7 is a flowchart showing the breakdown of tasks between the frontend and backend according to one embodiment.

FIG. 7 is a flowchart 70 showing the breakdown of tasks between the frontend and backend. After login, the front end fills in user demographic information and wellness data with compliance and importance data (operation 71). Next, the wellness data is sent to the server (operation 72). The backend evaluates the status of each wellness component (operation 73); identifies the most urgent component needed for action (operation 74); generates a recommendation for the most urgent component (operation 75); and creates a projection by PID to forecast the amount of improvement if the user follows the recommendation (operation 76). The frontend then displays the report (operation 77).

In the exemplified system, users will complete a checklist 79, such as that shown in FIG. 8, once a day (upon arising). The checklist will be collected at the Financial Counselor Check-ins and/or monthly recaps. The information being collected is only that which is required for the operation of the Centerline Wellness System.

Data Conformation for Human Instrumentation

Collecting data for assessing the physiological and financial aspects of wellness is fairly straightforward. More difficult is the characterization and collection of data for objectively assessing a user's psychological state.

Heart-Rate Variability (HRV) is regarded by many experts as an informative, non-invasive, passively accessible physiological indicator of psychological stress. It also carries information about physical activity in terms of tempo and intensity, which can be used to infer sleep and activity cycles. For this reason, the exemplified system uses HRV as a salient indicator of psychological wellness.

Continuous HRV monitoring can be done in a variety of ways. In recent years, a variety of devices for this purpose have been produced for direct sale to the general public. These wearable devices include chest strap monitors, wrist-mounted monitors, and monitors worn as rings. While chest straps are the most accurate and are relatively inexpensive, they have not enjoyed widespread popularity with the public. Most people would rather use a wrist-wearable device.

This variety of collection devices poses a possible obstacle to adoption of systems that use HRV data. Existing devices themselves are very different in quality, operation, and cost. Any add-on system that relies upon HRV data must accommodate this variation, since users are unlikely to adopt a system that requires them to purchase a new monitoring device.

Figure 9:
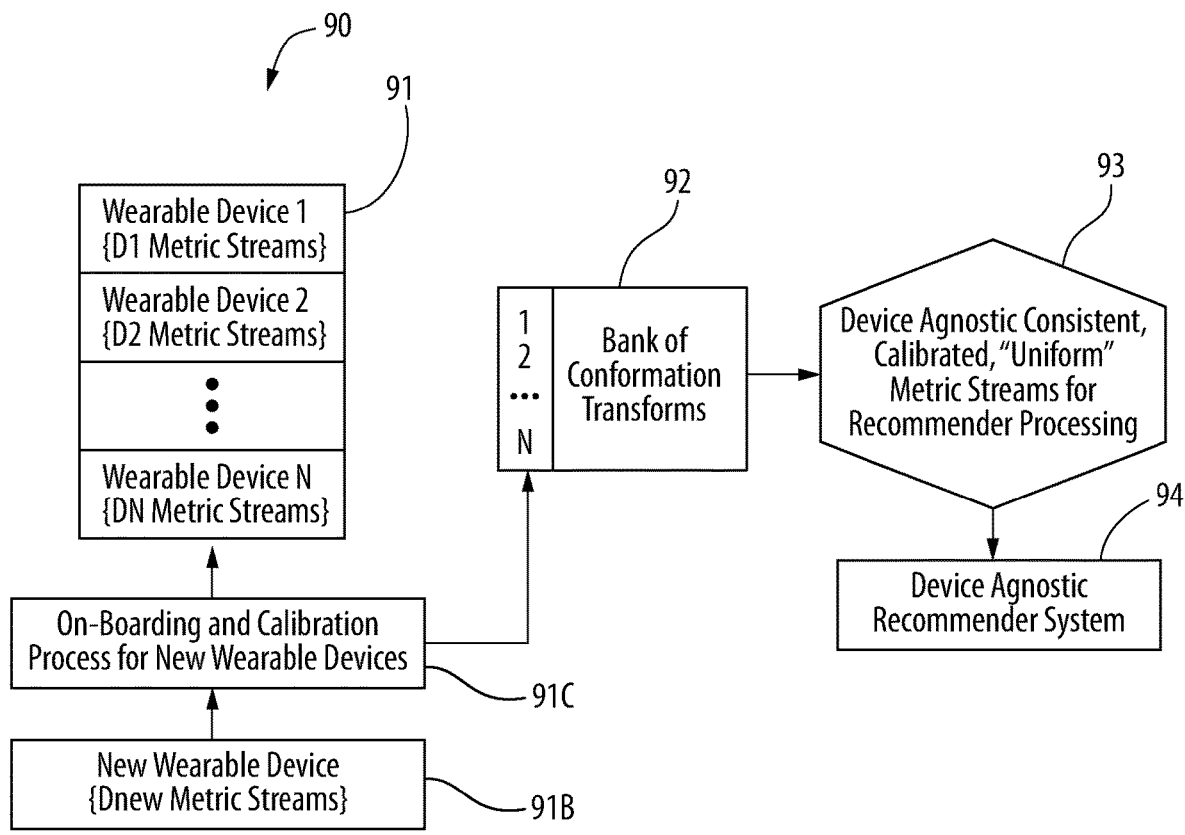
FIG. 9 is a block diagram of a device-agnostic frontend according to one embodiment.

FIG. 9 shows a device-agnostic frontend 90 for solving this problem. The frontend 90 ingests data from a wide range of devices 91, including new devices 91B requiring onboarding (operation 91C), and uses a bank of conformation transforms 92 to conform the data to device-agnostic data 93 for subsequent processing by the Recommender 94. The exemplary transform 92 has been calibrated using data collected in a live trial for a variety of input devices. The conformation transform uses a multi-variate regression (parameterized radial basis function, RBF).

Ground truth data may be collected by instrumenting a "standardizing user" with a chest strap heart rate monitor. These devices achieve high accuracy by monitoring cardio-electric signals by direct contract through the chest wall. Simultaneously, the standardizing user wears various wrist-mounted heart monitors. The concomitant data serve as the independent and dependent variables for the regression, respectively. The RBF is numerically optimized to transform the wrist data (which is of variable sampling rate, sensitivity, precision, bio-coupling effectiveness, etc.) to best estimates of the corresponding chest-strap data.

The following is a sample report generated automatically by the system:

ANTONE MCMAHON is a 31-year-old single male.

Evaluation Report
Financial State
ANTONE MCMAHON's overall financial wellness level is 0.004, which is at the Centerline for his demographic.
He has reached or exceeded Centerline Financial Wellness in 8 out of 10 areas.
The Financial Wellness factors that meet or exceed the centerline for his demographic are:

| Assessment | Value | Z-Score | Set Point | Importance | Compliance |
|---|---|---|---|---|---|
| A medium level of annual income is fine: | 31.1 | −0.485 | 35.002 | 0.848 | 0.881 |
| A medium level of short save is fine: | 0.057 | 0.337 | 0.05 | 0.681 | 0.796 |
| A medium level of long save is fine: | 0.461 | −0.173 | 0.496 | 0.257 | 0.235 |
| A medium level of college debt is fine: | 28.875 | −0.383 | 31.786 | 0.876 | 0.812 |

-continued

| ANTONE MCMAHON is a 31-year-old single male. | | | | | |
|---|---|---|---|---|---|
| A medium level of unsec debt is fine: | 5.785 | 0.086 | 5.218 | 0.544 | 0.248 |
| A medium level of credit score is fine: | 603.143 | −0.282 | 610.03 | 0.671 | 0.151 |
| A medium level of life insure is fine: | 0.995 | −0.022 | 1.003 | 0.501 | 0.758 |
| A low level of mortgage debt is good: | 11.517 | −1.293 | 100.995 | 0.539 | 0.222 |

His Financial Wellness factors that need improvement are:

| Assessment | Value | Z-Score | Set Point | Importance | Compliance |
|---|---|---|---|---|---|
| A low level of health insure is not healthy: | 0.751 | −0.612 | 1.0 | 0.325 | 0.793 |
| A low level of budgeting is not healthy: | 0.411 | −1.444 | 1.011 | 0.682 | 0.756 |

Physical State
ANTONE MCMAHON'S overall physical wellness level is −0.112, which is under the Centerline for his demographic.
He has reached or exceeded Centerline Physical Wellness in 9 out of 10 areas.
The Physical Wellness factors that meet or exceed the centerline for his demographic are:

| Assessment | Value | Z-Score | Set Point | Importance | Compliance |
|---|---|---|---|---|---|
| A medium level of bmi is fine: | 22.07 | 0.087 | 21.554 | 0.178 | 0.783 |
| A medium level of wb sugar is fine: | 92.474 | 0.914 | 84.864 | 0.605 | 0.963 |
| A medium level of act hr is fine: | 128.178 | −0.112 | 129.594 | 0.199 | 0.766 |
| A medium level of age is fine: | 31.588 | −0.203 | 31.588 | 0.171 | 0.216 |
| A medium level of tot cals is fine: | 2711.334 | 0.971 | 2395.075 | 0.484 | 0.177 |
| A medium level of carb cals is fine: | 497.583 | 0.593 | 402.509 | 0.563 | 0.202 |
| A very high level of bp diastolic is quite unhealthy: | 97.501 | 2.131 | 79.816 | 0.171 | 0.765 |
| A very low level of resting hr is quite unhealthy: | 45.935 | −3.184 | 71.723 | 0.207 | 0.248 |
| A very low level of sleeps is quite unhealthy: | 3.775 | −2.574 | 8.009 | 0.698 | 0.753 |

His Physical Wellness factors that need improvement are:

| Assessment | Value | Z-Score | Set Point | Importance | Compliance |
|---|---|---|---|---|---|
| A high level of bp systolic is not healthy: | 137.864 | 1.095 | 119.667 | 0.507 | 0.22 |

Psychological State
ANTONE MCMAHON'S overall psychological wellness level is −0.067, which is under the Centerline for his demographic.
He has reached or exceeded Centerline Psychological Wellness in 6 out of 10 areas.
The Psychological Wellness factors that meet or exceed the centerline for his demographic are:

| Assessment | Value | Z-Score | Set Point | Importance | Compliance |
|---|---|---|---|---|---|
| A medium level of positivity is fine: | 0.325 | 0.159 | 0.308 | 0.436 | 0.196 |
| A medium level of engagement is fine: | 0.585 | −0.105 | 0.61 | 0.397 | 0.784 |
| A medium level of meaning is fine: | 0.679 | 0.328 | 0.618 | 0.739 | 0.951 |
| A medium level of emo stability is fine: | 0.38 | −0.148 | 0.412 | 0.547 | 0.889 |
| A medium level of optimism is fine: | 0.368 | 0.258 | 0.323 | 0.411 | 0.17 |
| A medium level of resilience is fine: | 0.594 | −0.042 | 0.617 | 0.663 | 0.804 |

His Psychological Wellness factors that need improvement are:

| Assessment | Value | Z-Score | Set Point | Importance | Compliance |
|---|---|---|---|---|---|
| A low level of relationships is not healthy: | 0.291 | −0.89 | 0.513 | 0.408 | 0.842 |
| A low level of accomplishment is not healthy: | 0.011 | −1.873 | 0.309 | 0.463 | 0.155 |
| A low level of self esteem is not healthy: | 0.572 | −0.783 | 0.708 | 0.563 | 0.755 |
| A low level of vitality is not healthy: | 0.503 | −1.21 | 0.725 | 0.899 | 0.237 |

Recommendation Report
For domain financial, the significant issue area is budgeting:
Significance Score: 0.409
Importance to User: 0.682
User Compliance: 75.6%
Centerline Deviation: −0.6
Recommendations:
Increase: Plan! Develop weekly monthly and annual budgets you can live with. Be realistic but hold your resolve.
If your absolute essential expenses overshoot 50 percent of your income you may need to dip into the wants portion of your budget for a while. It's not the end of the world but you'll have to adjust your spending. Even if your necessities fall under the 50 percent cap revisiting these fixed expenses occasionally is smart. You may find a better cell phone plan an opportunity to refinance your mortgage or less expensive car insurance. That leaves you more to work with elsewhere.
Forecast:
If he follows the recommendation above, he may expect an 82.343% improvement in 5 weeks.
[projection visualization]
For domain physical, the significant issue area is bp_systolic:
Significance Score: 9.228
Importance to User: 0.507
User Compliance: 22.0%
Centerline Deviation: 18.197

| |
|---|
| ANTONE MCMAHON is a 31-year-old single male. |

Recommendations:
Decrease: Enroll in a gym for weekly exercise. Take an afternoon and evening walk. Spend less time on sedentary activities.
When it comes to resting heart rate lower is better. It usually means your heart muscle is in better condition and doesn't have to work as hard to maintain a steady beat. Studies have found that a higher resting heart rate is linked with lower physical fitness and higher blood pressure and body weight.
Forecast:
If he follows the recommendation above, he may expect a 92.892% improvement in 5 weeks.
[projection visualization]
For domain psychological, the significant issue area is relationships:
Significance Score: 0.09
Importance to User: 0.408
User Compliance: 84.2%
Centerline Deviation: −0.221
Recommendations:
Increase: Discuss relationships with someone older who cares about you. Read books about improving relationships.
Cuddling kissing hugging and sex can all help relieve stress. Positive physical contact can help release oxytocin and lower cortisol. This can help lower blood pressure and heart rate both of which are physical symptoms of stress. Interestingly humans aren't the only animals who cuddle for stress relief. Chimpanzees also cuddle friends who are stressed.
Forecast:
If he follows the recommendation above, he may expect a 73.517% improvement in 5 weeks.

Bias-Based Reasoning

While propositional and predicate logic are powerful reasoning tools, they do not mirror what human experts actually do, nor do decision trees, Bayesian analysis, neural networks, or support vector machines. Pose a problem for a human expert in their domain, and you will find, even given no evidence, that they have an a priori collection of beliefs about the correct conclusion. For example, a mechanic arriving at the repair shop on Tuesday morning already holds certain beliefs about the car waiting in Bay 3 before she knows anything about it. As she examines the car, she will update her prior beliefs, accruing "bias" for and against certain explanations for the vehicle's problem. At the end of her initial analysis, there will be some favored conclusions, which she will test, and so accrue more belief and disbelief. Without running decision trees, applying Bayes' Theorem, or using margin maximizing hyperplanes, she will ultimately adopt the conclusion she most believes is true. It is this "preponderance of the evidence" approach that best describes how human experts actually reason, and it is this approach we seek to model.

Bias-based Reasoning (BBR) is a mathematical method for automating implementation of a belief-accrual approach to expert problem solving. It enjoys the same advantages human experts derive from this approach; in particular, it supports automated learning, conclusion justification, confidence estimation, and natural means for handling both non-monotonicity and uncertainty. Dempster-Shafer Reasoning is an earlier attempt to implement belief-accrual reasoning, but suffers some well-known defects (Lotfi paradox, constant updating of parameters, monotonic, no explicit means for uncertainty). BBR overcomes these.

For simplicity and definiteness, the reasoning problem will be described here as the use of evidence to select one or more possible conclusions from a closed, finite list that has been specified a priori (the "Classifier Problem").

Expert reasoning is based upon facts (colloquially, "interpretations of the collected data"). Facts function both as indicators and contra-indicators for conclusions. Positive facts are those that increase our beliefs in certain conclusions. Negative facts are probably best understood as being exculpatory: they impose constraints upon the space of conclusions, militating against those unlikely to be correct. Facts are salient to the extent that they increase belief in the "truth", and/or increase "disbelief" in untruth.

A rule is an operator that uses facts to update beliefs by applying biases. In software, rules are often represented as structured constructs such as IF-THEN-ELSE, CASE, or SWITCH statements. Rules consist of an antecedent and a multi-part body. The antecedent evaluates a BOOLEAN expression; depending upon the truth-value of the antecedent, different parts of the rule body are executed.

As is typical with heuristic reasoners, BBR allows the complete separation of knowledge from the inferencing process. This means that the structure can be retrained, even repurposed to another problem domain, by modifying only data; the inference engine need not be changed. An additional benefit of this separability is that the engine can be maintained openly apart from sensitive data.

After applying a set of rules to a collection of facts, beliefs and disbeliefs will have been accrued for each possible conclusion (classification decision). This ordered list of beliefs is a belief vector. The final decision is made by examining this vector of beliefs, for example, by selecting the class having the largest belief-disbelief difference (but we will formulate a better adjudication scheme below).

There are two major problems to be solved; these are, in a certain sense, "inverses" of each other. First, the Adjudication Problem is reasoning forward from biases to truth. What is the proper algorithm for combining accrued positive and negative biases into an aggregate belief vector so that a decision can be made? Second, the Learning Problem is reasoning backwards from truth to biases.

Conventional parametric methods (e.g., Bayesian Inferencing), compute class likelihoods, but generally do not explicitly model "negative" evidence. Rather, they increase likelihoods for competing answers. They are inherently "batch" algorithms, performing their analysis after all evidence has been presented. They have the nice characteristic that they are capable of directly modeling the entire joint distribution (though this is rarely practical in actual practice). Their outputs are usually direct estimates of class probabilities.

Bias-based Reasoning (BBR) does not model the entire joint-distribution, but begins with the assumption that all facts are independent. This assumption is generally false for the entire population. This is effectively handled by segmenting the population data into strata within which independence holds approximately; rules are conditioned to operate within particular strata. BBR supports both batch and incremental modes. It can "roll up" its beliefs after all evidence has been collected, or it can use an incremental aggregation rule to adjusts its bias with respect to each class as evidence is obtained.

The following are desirable properties for a BBR: (1) Final conclusions should be independent of the order in which the evidence is considered. (2) The aggregation rule should have compact range, e.g., it must have no gaps, and there must be a maximum and minimum bias possible. (3) A bias of zero should mean that evidence for and against an answer are equal. (3) Symmetric Non-monotonic reasoning should be supported, that is, it should be possible to withdraw facts previously asserted and obtain the same result as if these facts had never been considered. (Symmetry is understood as accruing an amount of belief/disbelief and then accruing the same amount of disbelief/belief should leave the aggregate belief unchanged.)

The term Adjudication Rule (AR) is used for any method of combining a vector of positive beliefs with a vector of negative beliefs to obtain a belief vector from which a decision can be made by selecting the class having the greatest belief. This final belief vector is said to be adjudicated.

When there are many classes and many rules, the simple aggregation rule may be written as follows: Suppose that N belief heuristics and M disbelief heuristics have fired. The aggregate belief and disbelief for class k is:

$$B_k(\beta_{1k}, \ldots, \beta_{Nk}) = 1 - \Pi_{i=1}^{N}(1-\beta_{ik})$$

$$D_k(\delta_{1k}, \ldots, \delta_{Mk}) = 1 - \Pi_{j=1}^{M}(1-\delta_{jk})$$

An aggregated belief vector could be formed by looking at excess belief over disbelief by differencing:

$$\beta_{1k}, \beta_{2k}, \ldots, \beta_{Nk}, \delta_{1k}, \delta_{2k}, \ldots, \delta_{Mk}) = (B_1-D_1, B_2-D_2, \ldots, B_L-D_L)$$

The variable C is used to indicate that these differences are not class probabilities, but class "confidences" having no particular normalization properties. The properties of C are all attributes of the aggregation rule, the algorithm for combining positive and negative biases into a final L-dimensional vector of the beliefs for the L classes.

These aggregation formulae having the following properties: (1) They can be computed in a "batch method" as above, but they can both also be accumulated incrementally as evidence is gathered by newvalue=oldvalue+bias*(1-oldvalue). This allows individual rules to accrete belief, so that the computation of the belief vector is a side-effect of the rule firing process. (2) This rule has compact range=[0, 1]. (3) This rule is C-infinity (partial derivatives are computed below). (3) If a bias of 0 is accrued, the old belief is not changed; if a bias of 1 is accrued the belief is 1, and will never decrease. It provides no natural mechanism for handling uncertainty First is introduced the mechanism for non-monotonicity. Suppose that N belief heuristics having magnitudes $\beta_{k1} \geq 0$ and M disbelief heuristics having magnitudes $\delta_{jl} \geq 0$ have been applied. Rather than differencing belief and disbelief, we use a quotient in the accrual is used. The aggregated bias with respect to class l is defined:

$$B_l(\beta_{1,l}, \ldots, \beta_{N,l}, \delta_{1,l}, \ldots, \delta_{M,l}) = 1 - \left(\frac{\prod_{k=1}^{N}(1-\beta_{kl})}{\prod_{j=1}^{M}(1-\delta_{jl})}\right)$$

Then the aggregated belief vector is:

$$\bar{B}(\delta_{1,l}, \ldots, \delta_{N,1}, \delta_{1,l}, \ldots, \delta_{N,1}) = (B_1, \ldots, B_L)$$

$B_k$ is the adjudicated belief in hypothesis k. This expression for $\bar{B}$ is clearly symmetric in its arguments, so belief and disbelief can be accrued in any order. Further, accruing a belief of b followed by accrual of a disbelief of b will place a (1-b) term in both numerator and denominator of the quotient, which will divide out. This allows changes to belief from previous fact to be backed-out.

How do we determine the amount of belief, $\beta_{kl}$, and the amount of disbelief, $\delta_{jl}$, to accrue for each class in each heuristic? The components of $\bar{B}$ are differentiable with respect to the beliefs and disbeliefs, so the gradient may be computed:

$$\partial B_l/\partial \beta_{\bar{k}l} = \left(\frac{1}{1-\beta_{\bar{k}l}}\right)\left(\frac{\prod_{k=1}^{N}(1-\beta_{kl})}{\prod_{j=1}^{M}(1-\delta_{jl})}\right)$$

$$\partial B_l/\partial \beta_{\bar{j}l} = \left(\frac{-1}{1-\delta_{\bar{j}l}}\right)\left(\frac{\prod_{k=1}^{N}(1-\beta_{kl})}{\prod_{j=1}^{M}(1-\delta_{jl})}\right)$$

These can be compactly rewritten:

$$\partial B_l/\partial \delta_{\bar{k}l} = \frac{1-B_l}{1-\beta_{\bar{k}l}}$$

$$\partial B_l/\partial \delta_{\bar{j}l} = -\frac{1-B_l}{1-\delta_{\bar{j}l}}$$

These might make feasible optimization by a gradient technique, e.g., the Method of Steepest Descent:

$$\beta_{kl} = \beta_{kl} - h_{1kl}(\partial B_l/\partial \beta_{kl}), h_{1kl} \in \mathfrak{R}^+$$

$$\delta_{jl} = \delta - h_{2kl}(\partial B_l/\partial \delta_{jl}), h_{2kl} \in \mathfrak{R}$$

Figure 10:
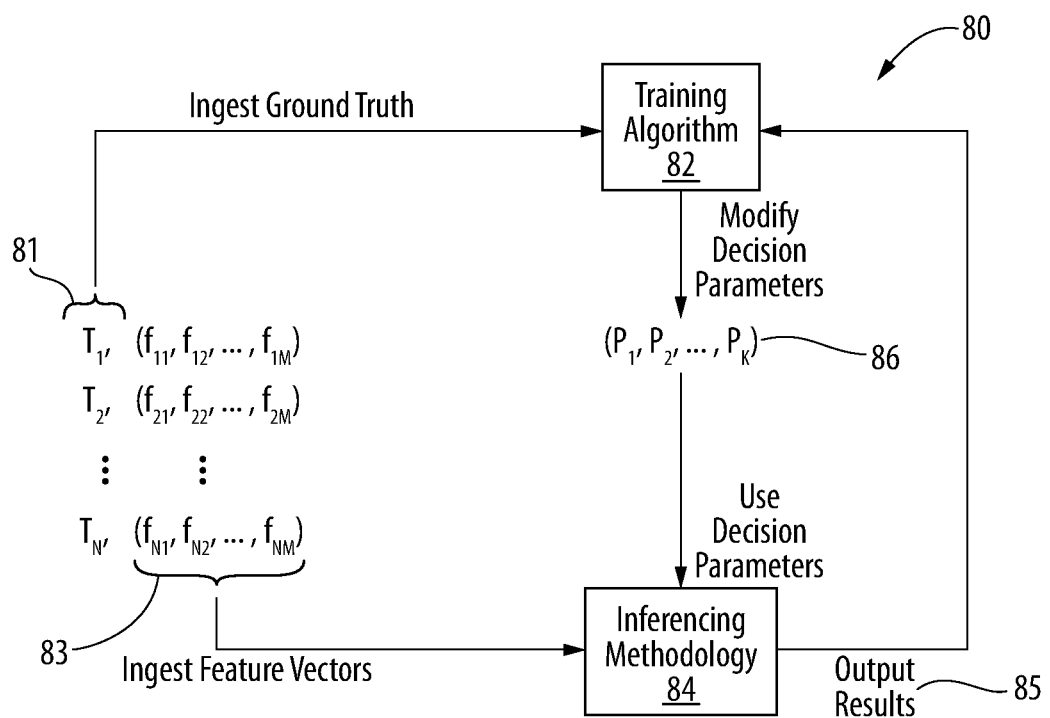
FIG. 10 is a block diagram of an iterative cycle using an update according to one embodiment.

FIG. 10 is a block diagram of an iterative cycle 80 using an update rule. A set of data having ground truth tags 81 are ingested by the training algorithm 82. Feature vectors 83 of the set of data, as well as decision parameters 86, are ingested by the inferencing methodology 84. The output results 85 of the inferencing methodology 84 are then fed to the training algorithm 82. The training algorithm 82 then modifies the decision parameters 86 fed to the inferencing methodology 84. The iterative cycle can be used to learn the beliefs and disbeliefs that will cause the heuristics to give correct answers on the training set.

Taking as a starting point the bias-based non-monotonic theory of the previous section, we finally introduce the mechanism for accommodating uncertainty. The goals are (1) use an estimate of the level of certainty to adjust the impact a fact can have on beliefs, and (2) provide a means for retrospectively changing the uncertainties of facts already applied, and updating current beliefs accordingly Uncertainty is an attribute of both the data source and the data itself ("good" sources sometimes provide bad data, for example). This means that our uncertainty mechanism must allow the assignment of "credibility" at the data-source level, and also to individual data from whatever source. All of the nice properties of the previous aggregation and adjudication rules are preserved (with one exception), and both non-monotonicity and accommodation of dynamic uncertainty are accommodated by the batch algorithm.

Suppose that there are M possible conclusions for the reasoner (e.g., M classes to which an entity is to be assigned). Let facts be interpreted and mapped to ordered 4-tuples, which we call fact vectors: $F_k=(s_k, t_k, c_k, V_k)$. Here the $k^{th}$ fact $F_k$ is from source $s_k$, with date-time-group $t_k$, a level of uncertainty, and a corresponding vector of features (=data measurements).

A Fact Base is a set of fact vectors $F=\{F_1, F_2, \ldots, F_L\}$. The fact base is a catalog of what we have been told by our sources with variable certainty at various times. A source is the originator of a fact. It could be a data collection system, data base, algorithm, manual estimate, etc. Each fact has a time $t_k$. This is provided to give recency and latency information, but also so that facts with particular times can have their certainties updated as a group. For example, it might be useful to retrospectively change the certainty level of all facts from a given source for given times, updating current beliefs accordingly.

Each fact has a certainty $c_k$ at time $t_k$. This is a numeric value between 0.0 and 1.0 inclusive. Facts that are "completely uncertain" have c=0. Facts that are "completely certain" have c=1. (In actual practice, these extreme values are unrealistic.) Intermediate levels of uncertainty fall between 0 and 1, with larger values indicating higher levels of confidence that the fact is actually true. The input to a KBES is a fact base. The Inference Engine selects facts to be processed and rules to fire so that beliefs are updated in accordance with the IE' s inferencing strategy. To fire, a rule invoked by the IE evaluates its predicate at the given fact and apply its biases $(\beta_{j1}, \beta_{j2}, \ldots, \beta_{jM})$, thereby adjusting beliefs in the some or all of the possible conclusions 1, 2, ... j, ..., M. The biases are applied using the aggregation rule.

The finalized theory demands symmetry: biases can be either positive or negative. Positive biases increase belief, while negative biases decrease belief. Two additional definitions are needed. (1) The Sgn Function (SIGNUM, SIGN, or SGN function) returns the algebraic sign of a real number: Sgn(x)=−1 if x is negative, otherwise+1. (2)$\gamma_s$ is the "gain" of source s. It is a value in [0,1] that is applied to all facts from source s, in addition to the confidences $c_j$ of facts from source s. It provides a source-specific "credibility tuning" value that will generally be set to 1. Possible applications will be mentioned below.

The finalized theory places a number of functional requirements specifically related to uncertainty on the aggregation rule: (U1) Facts firing with c=1 provide the full update effect of their biases, $B_{jki}$. (U2) Facts firing with c=0 have no effect on beliefs. (U3) Facts firing with intermediate values of c have intermediate effect, with larger c values having greater effect. (U4) Facts from sources having 7=1 provide the full update effect of their biases including the application of their c values. (U5) Facts from sources firing with γ=0 have no effect on beliefs. (U6) Facts from sources firing with intermediate values of γ have intermediate effect (including the application of their c values), with larger γ values allowing greater effect. In summary, c mitigates the impact of individual facts, while γ mitigates the impact of all facts from a given source.

In view of the foregoing, the NMBBRUU Aggregation Rule for batch mode (all biases for each class have been determined) may be stated as follows. Suppose that M belief heuristics for a particular conclusion k have been applied. Some of the biases $\beta_{kj}$ are positive and some are not. Further, suppose that the confidence associated with the $k^{th}$ fact is $c_k$, and the gain of the source for the $k^{th}$ fact is $\gamma_{sk}$. The aggregated bias with respect to class k for the fact base is defined:

$$B_k = 1 - \prod_{j=1}^{N}\left[\frac{1-|\beta_{kj}|}{1-\gamma_{s_k}(1-c_k)|\beta_{kj}|}\right]^{sgn(\beta_{kj})}$$

Then the aggregated belief vector is:

$\bar{B} = (B_1, \ldots, B_L)$

As before, $B_k$ is our adjudicated belief in hypothesis k. Note that the purpose of the sgn function is to put negative beliefs into the denominator so they can "cancel" positive beliefs. This incremental aggregation function satisfies all of the functional requirements for uncertainty processing. To back out a previously assigned fact having uncertainty $C_s$ and update current beliefs with revised uncertainty $\tilde{C}_s$, apply the following correction:

$$NewB = (1-OldB)\left(\frac{1-\gamma_k(1-c_s)|\beta_k|}{1-\gamma_k(1-\tilde{c}_s)|\beta_k|}\right)^{sgn\,\beta_k}$$

This changes the current belief to what it would have been had fact k been fired with updated uncertainty $\tilde{C}_s$.

Many useful capabilities can be provided using the approach described here, including the creation of confidence factors for conclusions, the automatic generation of conclusion justification reports that explain the reasoners conclusions in natural domain terms, and automatic trainability (offline learning). A particularly provocative application is the evaluation of the relative utility of information sources. It is possible that this could enable the detection of compromised sources (those that are providing low-quality information, or disinformation). This capability uses the source gain $\gamma_s$. By measuring the source-by-source sensitivity of reasoning quality, sources whose facts degrade overall performance can be identified. If "turning down the gain" on a source reduces overall system error, that source should be scrutinized. Source gain sensitivity could provide a systematic method for identifying bad input, whether it arises from a bad system input, or a trusted source that has been compromised. Source gain sensitivity could provide a systematic method for identifying bad input, whether it arises from a bad system input, or a trusted source that has been compromised.

Repurposing the Quality Adjusted Life Year (QALY)

Objective numeric "quality of life" metrics can be combined with the associated treatment costs to carry out a principled cost-benefit analysis for assessing and comparing treatments. Such metrics can also be repurposed using advanced analytic methods (e.g., machine learning) to build personalized recommender systems to help individuals assess and optimize their wellness as a life process. One such metric is the Quality Adjusted Life Year (QALY). Below is discussed a method for refining and extending QALY to the Extended Quality of Life Year (EQALY).

A subject's life can be modeled as a sequence of state vectors through time. The components of these state vectors are measures of wellness in different areas (e.g., psychological, physical, and financial metrics). These are referred to as wellness vectors. The space of all such vectors is a Euclidean space referred to as wellness space. A time sequence of wellness vectors constitutes a trajectory through wellness space that is referred to as the subject's lifeline.

Projecting lifeline vectors onto their components yields component lifelines: separate trajectories for each wellness component. A time sequence of component lifelines can be combined to produce a single numeric measure summarizing a subject's wellness along the corresponding component lifeline. This is a data fusion operation referred to herein as adjudication.

The standard QALY model employs a single quality value over a time interval measured in years. This gives a numeric rating for the quality of an individual's life over that interval (typically one year). The QALY can be regarded as a quantitative measure of disease burden, including both the quality and quantity of life. As such, the QALY is often used in healthcare to assess the economic value of medical interventions. One QALY equates to one year lived in perfect health.

To generalize the standard QALY, let Q denote a numeric measure of the subject's quality of life that is constant for a period of time T (in years). If T is one year, then the standard QALY equals Q. By allowing T to assume arbitrary values, it is possible to aggregate quality-of-life over arbitrary periods. The total accumulated quality of a life, or QALY, is Q×T. Essentially, the existing QALY method uses Riemann sums to infer the curve of wellness trajectories. The standard QALY calculates a wellness estimation as a uniform block, akin to a coarse Riemann sum, where quality of life (Q) is constant over time (T).

The QALY is an innovative insurance standard for measuring the human quality of life. However, the QALY suffers from low fidelity due to the twists and turns inherent in human lives and its low number of samples. A high-fidelity, objective QALY based on data collected from wearable technology and psychological self-reported data could summarize psychological, physical, and financial wellness. This QALY parameterizes a subject's path through wellness and helps to inform optimal fitness decisions.

In the real world, life circumstances and wellness vary over time. With a small sample size, random noise can mask the true quality of life and misinform readings. This coarse approach to the QALY could drastically misinterpret a single bad day. For example, it might fail to differentiate between a subject who struggles with chronic depression and one who went through a difficult breakup that week.

Figure 11:
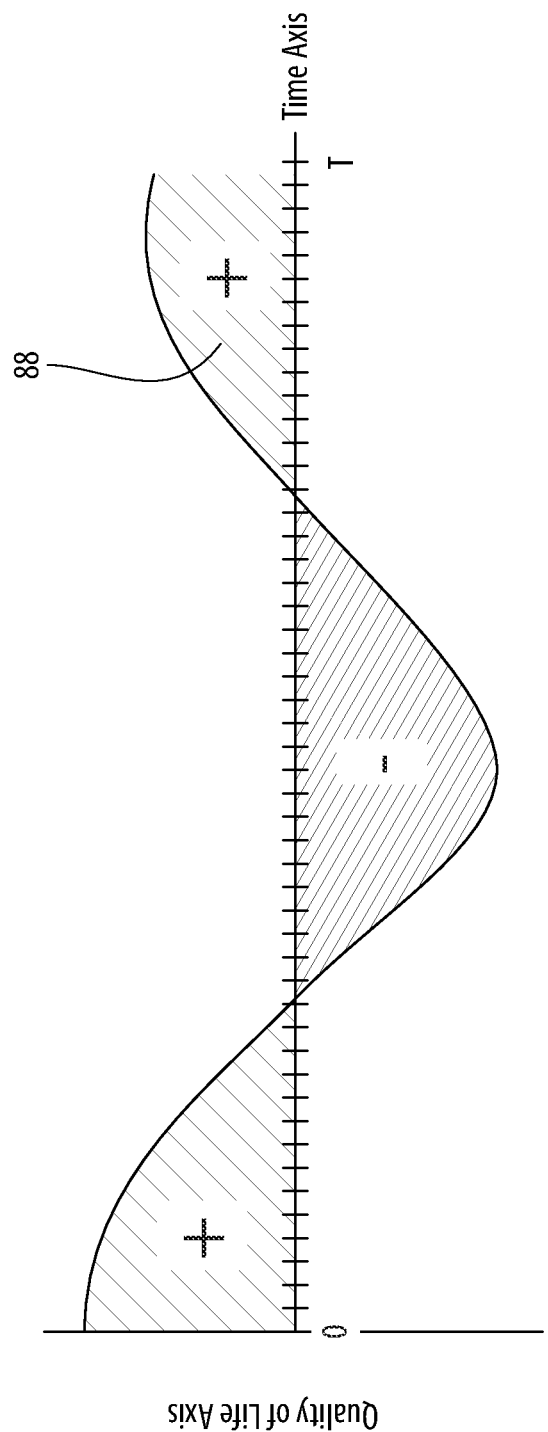
FIG. 11 is a graph of the aggregate summary EQALY as a Riemann Integral according to one embodiment.

FIG. 11 is a graph of EQALY 88 that accommodates both arbitrary sampling rates and variable quality measures by viewing the aggregate summary EQALY 88 as a Riemann Integral. EQALY 88 can vary smoothly, rather than remaining constant between large jumps. The sampling methodology uses frequent manual and instrumented feedback to determine may Q-values close in time for essentially continuous estimation of the quality of life. In this way, Q becomes not a discrete sequence of constants, but a piecewise-continuous function of time, Q(t). Using the QALY-as-an-area paradigm, this QALY model is moved from discrete, "chunky" sums to a Calculus-based Riemann Integral model:

$$QALY = \int_0^T Q(t)dt$$

As discussed above, wellness components can be placed into three categories: psychological, physical, and financial. Different wellness components can interact in complex ways that affect overall wellness. Examples of different wellness components are discussed above.

Figure 12:
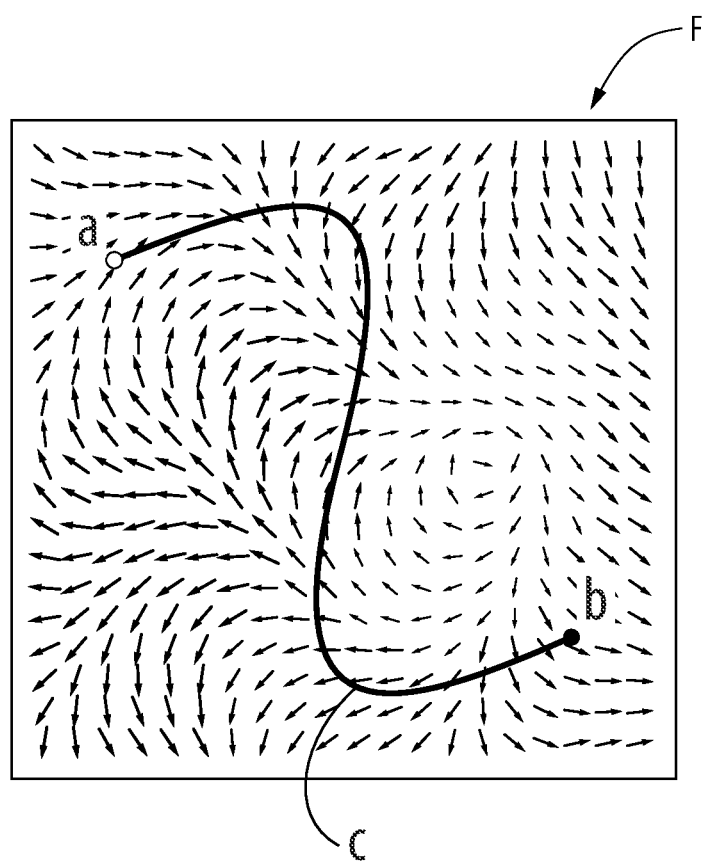
FIG. 12 shows the life of an individual modeled as a trajectory through wellness space according to one embodiment.
Figure 13:
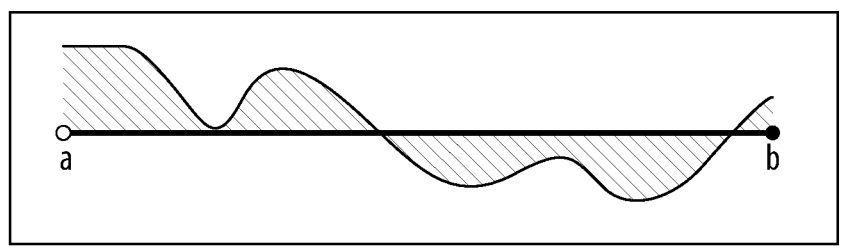
FIG. 13 is a graph showing the individual of FIG. 12 at position r(t) moving from state a to state b over time.

FIG. 12 shows the life of an individual modeled as a trajectory through wellness space. The wellness vector field F (components of quality, Q) are indicated by the arrows. The resulting field is called F. The life trajectory is represented by curve C. The individual at position r(t) at time t moves from state a to state b, as shown in FIG. 13. Their QALY is accumulated as they traverse C.

At each point in a life trajectory, an individual will make choices that tend to increase or decrease wellness in one or more wellness components. The aggregate effect of these choices is reflected in their EQALY over the resulting trajectory through wellness space.

In the exemplified embodiment of this section, to separately quantify the impact of each of the thirty wellness features used for quality assessment, the system uses four parameterizable weighting functions (discussed below). Each wellness component has its quality weighting function and parameters established by expert judgment. These weighting functions establish a scalar field for each corresponding wellness component. That is, each wellness value has an associated numeric weight. The quality-weighted time sequence of wellness values can then be aggregated as contour integrals along each projected component lifeline.

As an example, consider one of the wellness components in the model, Body Mass Index (BMI). Let a subject have a sequence of BMI values at time samples Ti (not necessarily a uniform mesh):

$$(BMI(T1), BMI(T2), \ldots, BMI(Tm))$$

This time sequence of BMI values is the projected lifeline for this subject's BMI over the time interval [T1, Tm].

The exemplified system expresses wellness values as z-scores concerning a reasonable BMI demographic for the subject, registering the optimal BMI for the demographic at a z-score of zero. Thus, a BMI score of 1 would be one standard deviation above the optimal z-score of 0, a score of −1 one standard deviation below, and so forth. This process can be applied to any number of wellness components.

Figure 14:
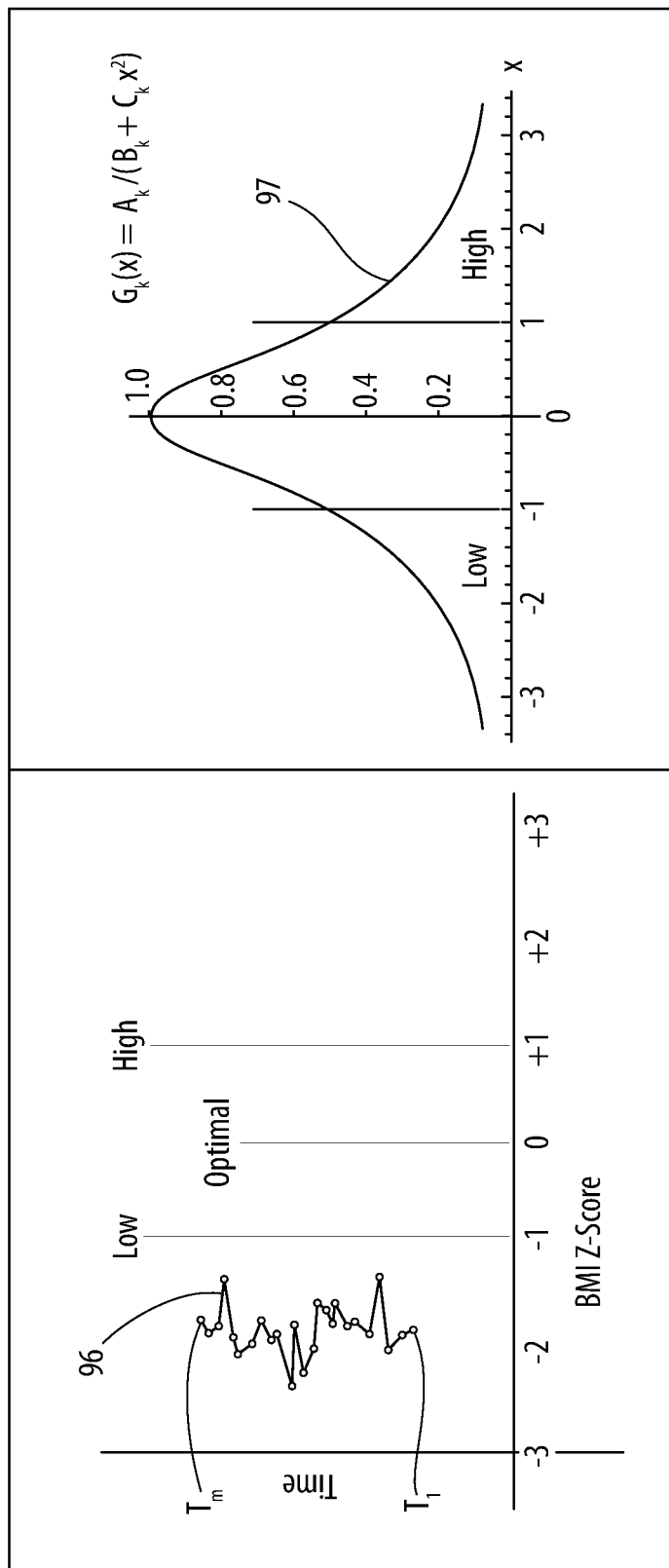
FIG. 14 provides a plot of BMI z-score, and a plot of a weighting function for BMI according to one embodiment.

FIG. 14 shows a plot 96 of BMI z-score, and a plot 97 of a weighting function for BMI. Plotting the pairs {BMI(Ti), Ti)} as in plot 96 shows the wellness lifeline for the subject in the wellness component Body Mass Index. It may be observed in plot 97 that the subject falls into the Low BMI region, which, once the weighting is applied, will result in a lower QALY value for the BMI component of the wellness vector.

The weighting function for the BMI example is roughly normal. The highest quality is at z-score=0, while wellness quality is lower as the BMI falls below or rises above the optimum. The weighting function may be expressed as $G_k(x) = A_k/(B_k + C_k x^2)$, having tunable parameters $A_k$, $B_k$, and $C_k$.

The same quality weighting function is used for all time samples. This establishes a scalar field in the BMI×Time-space. Weighting is applied to each BMI sample by evaluating the weighting function at the corresponding BMI value, giving the component quality $Q_k = G_k(BMI)$. The line integral along this trajectory through the scalar field sums the BMI quality over the entire lifeline.

$$Q_k = \oint G_k dS = \oint G_k(r_k(t))ds = \oint G_k(r_k(t))|r_k'(t)|dt$$

The trajectory is the piecewise linear path parametrized by rk(t), and Gk is the quality weighting function for this wellness component. In the exemplified system, a quality model has been selected for each of the thirty wellness components. Qk is the trajectory QALY for the kth wellness component, where k ranges from one to thirty. Parameterizations have been created for sixteen subject demographics (described below), establishing demographic cliques. These cliques can be used as collections of examples for supervised and unsupervised learning, collaborative filtering, and more.

The sixteen high-fidelity simulant demographics are defined in recognition of the fact that separate weighting models will be required for different subject demographics. Tuning for a demographic is accomplished by adjusting the weighting function parameters. The exemplified system uses eight demographics, splitting on age group, gender, and marital status.

In this way, separate quality models with their associated weighting schemes are established in each wellness area. Each wellness component (e.g., separately for Heart Rate Variance Stress Level, Body Mass Index, Total Unsecured Debt, etc.) has a corresponding time sequence of wellness values. Arranging these in an ordered array gives rise to a time sequence of wellness vectors in an N-dimensional (Euclidean) wellness space. Application of the weighting functions (by contour integration) obtains a vector of QALY's in each wellness component for the entire time sequence.

Figure 15:
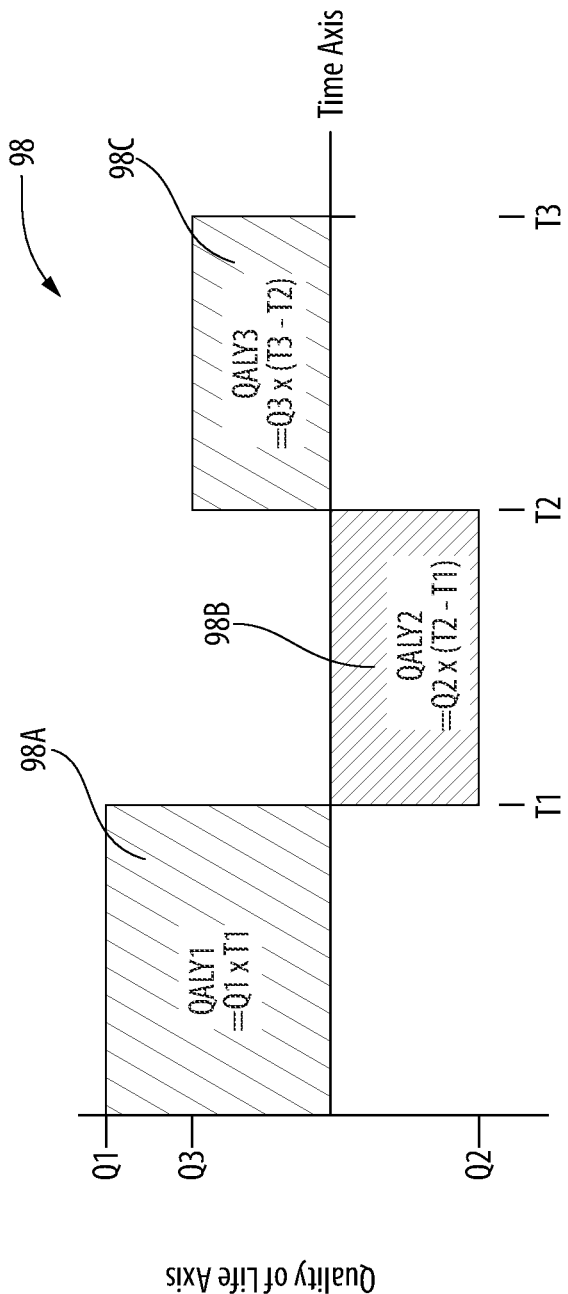
FIG. 15 is a graph of QALY over time.

FIG. 15 is a graph 98 of QALY over time. As shown, the discussed multi-factor QALY expects life to vary over time. A first period 98A represents a period of excellent wellness. A second period 98B represents a period of poor wellness. A third period 98C represents a period of moderate wellness. The total accumulated quality over the entire period is the sum of the accumulated qualities at each measurement. In the simple example below, generally high wellness balances out a difficult patch in the middle of the subject's life. Moreover, smart technology could allow an even more granular approach, for example, collecting data weekly.

The QALY is extended to a multi-factor model by translating wellness into multiple numeric components and computing a time sequence of qualities for each. The exemplified system transforms the resulting time sequence of QALY vectors to obtain an Extended Quality Adjusted Life Year or EQALY. The EQALY Model generalizes the time-sampling scheme for data collection and supports the introduction of arbitrary wellness measures into the QALY. This allows it to improve the fidelity and utility of the QALY so it can serve as a multi-factor, comprehensive wellness metric for a wide range of applications, including monitoring of current fitness, and prediction of future health risks.

While the standard QALY is computed as the product of a single quality metric and time duration, the EQALY is obtained by calculating a time sequence of QALY's in many wellness areas and adjudicating the resulting vector of QALY's to obtain a single numeric EQALY for the entire time sequence of wellness measurements (lifeline).

The inherent correlation and causal linkages among the indicators and metrics for the three wellness domains ("Mind, Body, and Balance Sheet") suggest the application of data fusion methods to formalize an integrated EQALY as a holistic wellness assessment for the subject. Using high-sample rate data collection methods described below, this EQALY can provide not just occasional point estimates, but high sample-rate life-lines of the subject through a Quality Space, Q.

In the exemplified software implementation, Q is a 30-dimensional Euclidean Space. The EQALY is computed as a high-fidelity fitness estimate using a contour integral along the lifeline of the subject through Q. Through periodic first-person checklists, advisor interviews, and bio-measurements from wearable devices, the system can obtain psychological, physical, and financial high sample-rate measurements.

FIG. 14 (discussed above) shows how the EQALY for a particular one of the thirty wellness features (Body Mass Index) is computed along the subject's lifeline as a contour integral. The portion of the contour used for this computation can be adjusted to suit applications. For example, a retrospective integral may be useful for hospital analysis. The weighted Quality contribution for BMI may be represented as the contour integral of the trajectory through time ("lifeline").

Figure 16:
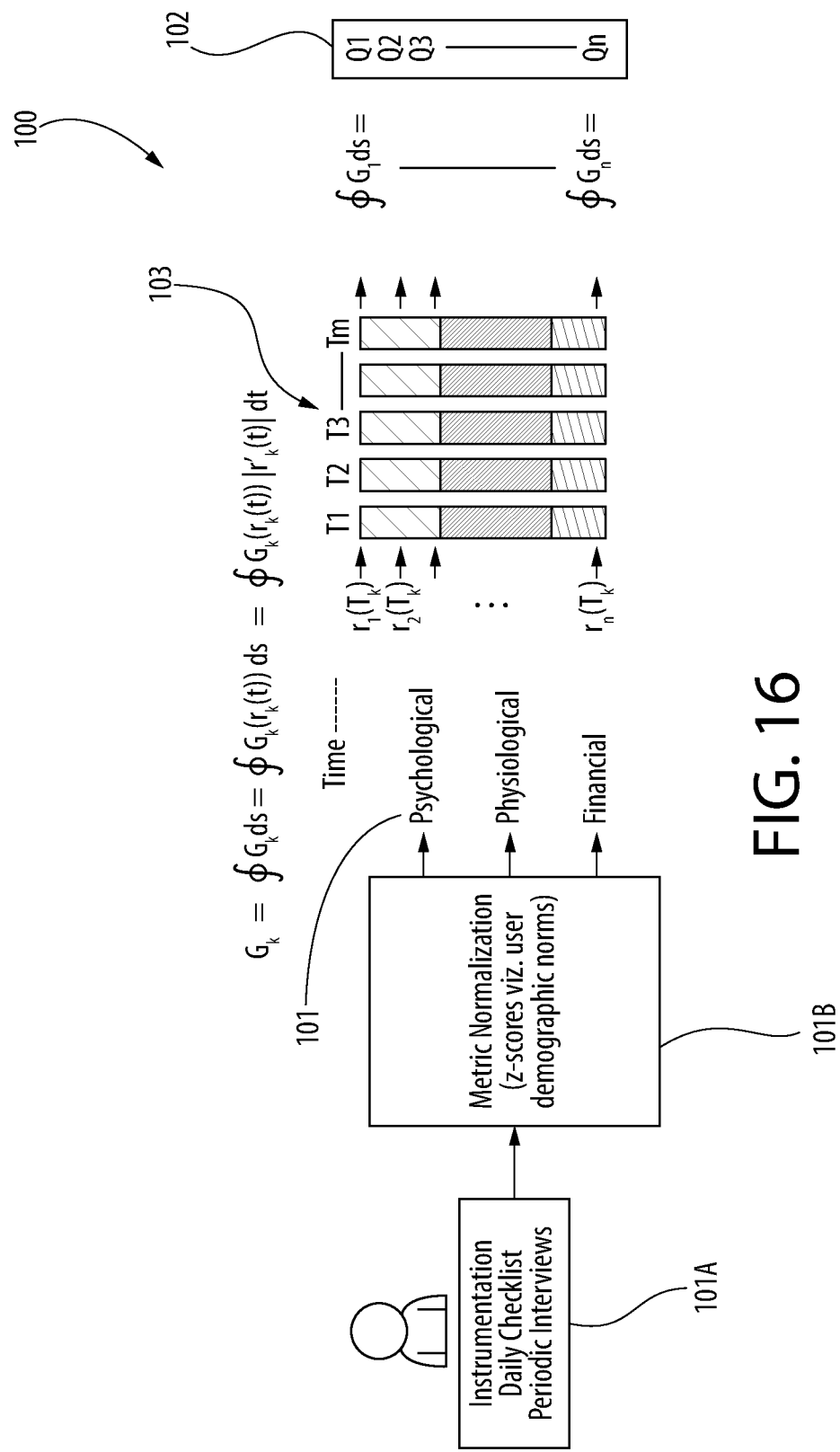
FIG. 16 is a flowchart showing how, according to one embodiment, the Multi-factor EQALY Process allows the system to integrate an arbitrary number of features into a single metric.

FIG. 16 is a flowchart 100 showing how the Multi-factor EQALY Process allows the system to integrate an arbitrary number of features into a single metric. The EQALY integrates separate measurements from the three wellness categories 101 into a single measurement 102. Various sources 101 provide data for normalization 101B. The vectors of wellness components at the sample times 103 are vertical tri-color bars (for the three wellness categories). The contour integrations are performed "horizontally" through time for each wellness component. The time sequence of vectors constitutes a health trajectory through the N-dimensional wellness space. The weighting function for each wellness component is established by demographic norms, expert knowledge, and human trials. Additionally, these weighting functions' parameters can modulate the relative impact of each wellness component. A graphical depiction of the EQALY process follows.

The vector $(B1, B2, \ldots, B_m)$ is the vector of importance values for each wellness component for this demographic. A Q-vector which is similar in direction to $B_m$ will have a large EQALY value, and vice versa. With its weighting, each component of the aggregate quality-of-life along a given trajectory can be computed as a line integral of the scalar field given by the weighting function for that component. This yields N component QALY's (one in each wellness component), giving an N component vector of QALY's for the entire time sequence ("trajectory") in the N-dimensional wellness space.

A metric transform is applied to the vector of QALY's to create an adjudicated EQALY for the entire trajectory. In one embodiment, the approach to adjudicating the QALY vectors for a trajectory is to compute the cosine distance between the QALY vector and a benchmark vector of optimum values for each wellness component. The closer the cosine distance is to 1, the higher the assigned EQALY. EQALY may be expressed as follow, where . denotes the standard vector inner product, and inclusion by vertical brackets denotes computation of the standard vector norm:

$$EQALY(\tau) = \mathrm{ArcCos}\left(\frac{Q1, Q2, \ldots, Qn) \cdot (B1, B2, \ldots, Bn)}{|(Q1, Q2, \ldots, Qn)||(B1, B2, \ldots, Bn)|}\right)$$

The EQALY benchmark vectors can be assigned differently based on demographic data. This is important because optimum wellness values and their associated weighting must be tuned for the demographics to which they are applied. In this way, the EQALY quantifies the aggregate wellness of the individual along a trajectory through the EQALY wellness space.

While the inventions have been described with respect to specific examples including presently preferred modes of carrying out the inventions, those skilled in the art will appreciate that there are numerous variations and permutations of the above described systems and techniques. It is to be understood that other embodiments may be utilized and structural and functional modifications may be made without departing from the scope of the present inventions. Thus, the spirit and scope of the inventions should be construed broadly as set forth in the appended claims.

What is claimed is:

1. A method for providing a recommended wellness behavior in real time, the method comprising:
   a) receiving, for a user, user data for different wellness components, the user data comprising:
      i) real-time device data obtained from a wearable device, the device data being indicative of a physical health status and a stress status of the user;
      ii) financial data for the user; and
      iii) psychological data for the user;
      iv) wherein the user data includes current data and historical data;
   b) receiving at least one user behavior preference indicative of a preferred recommended behavior;
   c) receiving demographic standards for the different wellness components;
   d) assessing the user's wellness by:
      i) for each wellness component, determining a current user score based on the received user data;
      ii) for each wellness component, determining a difference between the current user score and the demographic standard;
      iii) for each wellness component, using a recursive algorithm to:
         1) determine a predicted future score based on (a) the current user score; (b) the difference between the current user score and the demographic standard; and (c) a controller coefficient that depends on a demographic for the user; and
         2) determine a difference between the predicted future score and the demographic standard;
   e) identifying at least one recommended behavior to be performed by the user in real time, the identification being based on:
      i) an identification of the wellness components having greatest differences between the predicted future score and the demographic standard; and
      ii) the at least one user behavior preference;
   f) automatically causing the wearable device to provide the user an indicator of the at least one recommended behavior to be performed by the user in real time, the indicator comprising a haptic alert provided by the wearable device or a message displayed by the wearable device; and
   g) the user performing the at least one recommended behavior;
   h) wherein operations a) to f) are performed by one or more processors.

2. The method of claim 1:
   wherein the wellness components are grouped into at least one of three wellness categories, the wellness categories being psychological, physical, and financial;
   wherein the psychological wellness category comprises at least one of the following wellness components: positivity, engagement, relationships, meaning, accomplishment, emotional stability, optimism, resilience, self esteem, or vitality;
   wherein the physical wellness category comprises at least one of the following wellness components: weight, blood pressure, sugar, heart rate, age, sleep, diet; and
   wherein the financial wellness category comprises at least one of the following wellness components: spending less than income, timely bill-paying, sufficient liquid savings, sufficient long-term savings, manageable debt load, prime credit score, have appropriate insurance, and plan ahead for expenses.

3. The method of claim 1 wherein operations a) to f) are repeated in real-time.

4. The method of claim 1 wherein the recursive algorithm is carried out by a proportional-integral-derivative (PID) controller.

5. The method of claim 1 wherein each controller coefficient is different for each wellness component and is determined to scale an output of the controller.

6. The method of claim 1 wherein the identification of the recommended behaviors is further based on past user recommendations.

7. The method of claim 1 wherein the determination of the difference between the current user score and the demographic standard uses bias-based reasoning.

8. The method of claim 1 wherein the identification of at least one recommended behavior uses bias-based reasoning.

9. The method of claim 1 wherein the user behavior preferences comprises at least one of a preferred breathing technique or a preferred mindfulness exercise.

10. A method for providing a recommended wellness behavior, the method comprising:
    a) receiving, for a user, user data for different wellness components, the user data comprising:
       i) device data obtained from a wearable device, the device data being indicative of a physical health status or a stress status of the user;
       ii) financial data for the user; and
       iii) psychological data for the user;
    b) receiving demographic standards for the different wellness components;
    c) assessing the user's wellness by:
       i) for each wellness component, determining a current user score based on the received user data;
       ii) for each wellness component, determining a difference between the current user score and the demographic standard;
       iii) for each wellness component, determining a comparison score based on the current user score;
    d) identifying at least one recommended behavior to be performed by the user, the identification being based on an identification of the wellness components having greatest differences between the comparison score and the demographic standard;
    e) outputting an indicator of the at least one recommended behavior to be performed by the user; and
    f) the user receiving the indicator and performing the at least one recommended behavior;
    g) wherein operations a) to e) are performed by one or more processors.

11. The method of claim 10 further comprising receiving at least one user behavior preference indicative of a preferred recommended behavior, wherein the identification of the at least one recommended behavior is based on the at least one user behavior preference.

12. The method of claim 10:
    wherein device data obtained from the wearable device is real-time data;
    wherein operations a) to e) are repeated in real-time to provide the indicator of the at least one recommended behavior in real-time.

13. The method of claim 10 wherein the comparison score is a predicted future score, the predicted future score being determined based on:

the current user score;
the difference between the user score and the demographic standard; and
a controller coefficient that depends on a demographic for the user.

14. The method of claim 13 wherein the identification of the at least one recommended behavior is based on an identification of the wellness components having a greatest difference between the predicted future score and the demographic standard.

15. The method of claim 10 wherein the comparison score is the current user score.

16. The method of claim 10 wherein the comparison score is further based on previously-determined current user scores.

17. The method of claim 10 wherein the user data includes current data and historical data.

18. A system for providing a recommended wellness behavior in real time, the system comprising:
 a) a wearable device configured to obtain real-time device data indicative of a physical health status and a stress status of a user;
 b) a server configured to carry out the operations of:
  i) receiving user data for different wellness components, the user data comprising:
   1) the device data;
   2) financial data for the user; and
   3) psychological data for the user;
   4) wherein the user data includes current data and historical data;
  ii) receiving at least one user behavior preference indicative of a preferred recommended behavior;
  iii) receiving demographic standards for the different wellness components;
  iv) assessing the user's wellness by:
   1) for each wellness component, determining a current user score based on the received user data;
   2) for each wellness component, determining a difference between the current user score and the demographic standard;
   3) for each wellness component, using a recursive algorithm to: (a) determine a predicted future score based on (i) the current user score; (ii) the difference between the current user score and the demographic standard; and (iii) a controller coefficient that depends on a demographic for the user; and (b) determine a difference between the predicted future score and the demographic standard;
  v) identifying at least one recommended behavior to be performed by the user in real time, the identification being based on:
   1) an identification of the wellness components having greatest differences between the predicted future score and the demographic standard; and
   2) the at least one user behavior preference; and
  vii) automatically causing the wearable device to provide the user an indicator of the at least one recommended behavior to be performed by the user in real time, the indicator comprising a haptic alert provided by the wearable device or a message displayed by the wearable device.

19. A system for providing a recommended wellness behavior, the system comprising:
 a) a wearable device configured to obtain device data indicative of a physical health status or a stress status of a user;
 b) a server configured to carry out the operations of:
  i) receiving user data for different wellness components, the user data comprising:
   1) the device data;
   2) financial data for the user; and
   3) psychological data for the user;
  ii) receiving demographic standards for the different wellness components;
  iii) assessing the user's wellness by:
   1) for each wellness component, determining a current user score based on the received user data;
   2) for each wellness component, determining a difference between the user score and the demographic standard;
   3) for each wellness component, determining a comparison score based on the current user score;
  iv) identifying at least one recommended behavior to be performed by the user, the identification being based on an identification of the wellness components having greatest differences between the comparison score and the demographic standard; and
  v) outputting an indicator of the at least one recommended behavior to be performed by the user, wherein the user receives the indicator and performs the recommended behavior.

* * * * *